(12) United States Patent
Mayr et al.

(10) Patent No.: US 10,759,707 B2
(45) Date of Patent: Sep. 1, 2020

(54) ADDITIVE MANUFACTURING PROCESS FOR PRODUCING CERAMIC ARTICLES USING A SOL CONTAINING NANO-SIZED PARTICLES

(71) Applicant: 3M INNOVATIVE PROPERTIES COMPANY, St. Paul, MN (US)

(72) Inventors: Helmar B. Mayr, Kaufering (DE); Malte Korten, Moorenweis (DE); Christine M. Andres, Washington, DC (US); Brant U. Kolb, Afton, MN (US); Holger Hauptmann, Sindelsdorf (DE); Gallus Schechner, Herrsching (DE); Michael Jahns, Gilching (DE); Kathleen M. Humpa, Stillwater, MN (US); Melissa A. Lackey, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 247 days.

(21) Appl. No.: 15/574,630

(22) PCT Filed: May 18, 2016

(86) PCT No.: PCT/US2016/032986
§ 371 (c)(1),
(2) Date: Nov. 16, 2017

(87) PCT Pub. No.: WO2016/191162
PCT Pub. Date: Dec. 1, 2016

(65) Prior Publication Data
US 2018/0148378 A1    May 31, 2018

(30) Foreign Application Priority Data
May 28, 2015   (EP) .................................. 15169580

(51) Int. Cl.
*C04B 35/488* (2006.01)
*C04B 35/645* (2006.01)
(Continued)

(52) U.S. Cl.
CPC .............. *C04B 35/488* (2013.01); *A61C 5/77* (2017.02); *A61C 13/0004* (2013.01);
(Continued)

(58) Field of Classification Search
CPC ................ C04B 35/488; C04B 35/624; C04B 35/62655; C04B 35/645;
(Continued)

(56) References Cited

U.S. PATENT DOCUMENTS

| 4,575,330 A | 3/1986 | Hull |
| 5,453,262 A | 9/1995 | Dawson |

(Continued)

FOREIGN PATENT DOCUMENTS

| EP | 2151214 | 2/2010 |
| EP | 2157067 | 2/2010 |

(Continued)

OTHER PUBLICATIONS https://web.archive.org/web/20150227034621/https://minerals.usgs.gov/minerals/pubs/commodity/zirconiunn/USGS 20-27-2015 accessed on Jan. 25, 2019 (Year: 2015).*

(Continued)

*Primary Examiner* — Alison L Hindenlang
*Assistant Examiner* — Andrés E. Behrens Jr.
(74) *Attorney, Agent, or Firm* — 3M Innovative Properties Company

(57) ABSTRACT

The present invention relates to a process for producing a ceramic article, the process comprising the steps of providing a printing sol, the printing sol comprising solvent, nano-sized particles, radiation curable monomer(s) and pho- (Continued)

toinitiator, the printing sol having a viscosity of less than 500 mPa*s at 23° C., processing the printing sol as construction material in an additive manufacturing process to obtain a 3-dim article being in a gel state, the 3-dim article having a Volume A, transferring the 3-dim article being in a gel state to a 3-dim article being in an aerogel state, heat treating the 3-dim article to obtain a sintered 3-dim ceramic article, the ceramic article having a Volume F, Volume A of the 3-dim article in a gel state being more than 500% of Volume F of the ceramic article in its sintered state. The invention also relates to a ceramic article obtainable according to such a process. The ceramic article can have the shape of a dental or orthodontic article.

15 Claims, 3 Drawing Sheets

(51) Int. Cl.

| | | |
|---|---|---|
| C04B 35/632 | (2006.01) | |
| C04B 35/624 | (2006.01) | |
| C04B 35/486 | (2006.01) | |
| A61C 13/083 | (2006.01) | |
| A61C 13/09 | (2006.01) | |
| A61C 13/00 | (2006.01) | |
| B28B 1/00 | (2006.01) | |
| A61C 5/77 | (2017.01) | |
| B33Y 10/00 | (2015.01) | |
| C04B 35/626 | (2006.01) | |
| A61K 6/802 | (2020.01) | |
| A61K 6/807 | (2020.01) | |
| A61K 6/818 | (2020.01) | |
| A61K 6/822 | (2020.01) | |
| B33Y 70/00 | (2020.01) | |
| A61C 7/12 | (2006.01) | |
| B33Y 80/00 | (2015.01) | |

(52) U.S. Cl.
CPC ...... *A61C 13/0013* (2013.01); *A61C 13/0018* (2013.01); *A61C 13/0019* (2013.01); *A61K 6/802* (2020.01); *A61K 6/807* (2020.01); *A61K 6/818* (2020.01); *A61K 6/822* (2020.01); *B28B 1/001* (2013.01); *B33Y 10/00* (2014.12); *B33Y 70/00* (2014.12); *C04B 35/486* (2013.01); *C04B 35/624* (2013.01); *C04B 35/62625* (2013.01); *C04B 35/62655* (2013.01); *C04B 35/632* (2013.01); *C04B 35/645* (2013.01); *A61C 7/12* (2013.01); *A61C 13/0022* (2013.01); *A61C 13/083* (2013.01); *A61C 13/09* (2013.01); *B33Y 80/00* (2014.12); *C04B 2235/3206* (2013.01); *C04B 2235/3208* (2013.01); *C04B 2235/3217* (2013.01); *C04B 2235/3225* (2013.01); *C04B 2235/3227* (2013.01); *C04B 2235/3229* (2013.01); *C04B 2235/3244* (2013.01); *C04B 2235/449* (2013.01); *C04B 2235/528* (2013.01); *C04B 2235/5454* (2013.01); *C04B 2235/606* (2013.01); *C04B 2235/6023* (2013.01); *C04B 2235/6026* (2013.01); *C04B 2235/762* (2013.01); *C04B 2235/765* (2013.01); *C04B 2235/77* (2013.01); *C04B 2235/94* (2013.01); *C04B 2235/95* (2013.01); *C04B 2235/9615* (2013.01); *C04B 2235/9653* (2013.01)

(58) Field of Classification Search
CPC .... C04B 2235/3225; C04B 2235/3227; C04B 2235/3244; C04B 2235/528; C04B 2235/5454; C04B 2235/6026; C04B 2235/606; C04B 2235/77; C04B 2235/9653; B33Y 10/00; B33Y 70/00; A61C 13/0013; A61C 7/12; B28B 1/001
See application file for complete search history.

(56) References Cited

U.S. PATENT DOCUMENTS

| | | |
|---|---|---|
| 5,652,192 A | 7/1997 | Matson |
| 6,283,997 B1 | 9/2001 | Garg |
| 6,955,776 B1 | 10/2005 | Feenstra |
| 7,241,437 B2 | 7/2007 | Davidson |
| 7,429,422 B2 | 9/2008 | Davidson |
| 7,927,538 B2 | 4/2011 | Moszner |
| 8,003,040 B2 | 8/2011 | El-Siblani |
| 8,133,831 B2 | 3/2012 | Laubersheimer |
| 8,329,296 B2 | 12/2012 | Apel |
| 9,403,726 B2 | 8/2016 | Fischer |
| 2003/0222366 A1 | 12/2003 | Stangel |
| 2004/0094058 A1* | 5/2004 | Kasperchik ........... C04B 35/624 |
| | | 101/483 |
| 2007/0072762 A1 | 3/2007 | Neil |
| 2009/0321971 A1 | 12/2009 | Brodkin |
| 2010/0249305 A1 | 9/2010 | Laubersheimer |
| 2012/0010066 A1* | 1/2012 | Fischer ............... C04B 35/6346 |
| | | 501/32 |
| 2012/0308837 A1 | 12/2012 | Schlechtriemen |
| 2014/0183799 A1 | 7/2014 | Fischer |
| 2015/0079313 A1 | 3/2015 | Vogel-Martin |
| 2015/0157430 A1* | 6/2015 | Hauptmann ........... A61C 13/01 |
| | | 428/312.8 |
| 2015/0203650 A1* | 7/2015 | Kolb .................... A61C 13/082 |
| | | 428/220 |
| 2015/0258732 A1* | 9/2015 | Stampfl .................. B33Y 10/00 |
| | | 264/401 |
| 2018/0221119 A1* | 8/2018 | Jung ...................... B32B 18/00 |

FOREIGN PATENT DOCUMENTS

| | | |
|---|---|---|
| EP | 2404590 | 1/2012 |
| WO | WO 2001-13815 | 3/2001 |
| WO | WO 2008-083282 | 7/2008 |
| WO | WO 2009-085926 | 7/2009 |
| WO | WO 2013-055432 | 4/2013 |
| WO | WO 2015-038890 | 3/2015 |
| WO | WO 2016-140840 | 9/2016 |
| WO | WO 2016-191534 | 12/2016 |

OTHER PUBLICATIONS https://web.archive.org/web/20150217122251/https://en.wikipedia.org/wiki/Riboflavin Wikipedia article on Riboflavin from Feb. 15, 2015. Accessed on Jan. 25, 2019 (Year: 2015).*
Ebert, "Direct Inkjet Printing of Dental Prostheses Made of Zirconia", Journal of Dental Research, 2009, vol. 88, No. 7, pp. 673-676, XP002745570.
Mitteramskogler, "Light curing strategies for lithography-based additive manufacturing of customized ceramics", Additive Manufacturing, Oct. 2014, vol. 1-4, pp. 110-118, XP55225474.
Ozkol, "Potentials of the "Direct inkjet printing" method for manufacturing 3Y-TZP based dental restorations", Journal of the European Ceramic Society, 2014, vol. 32, pp. 2193-2201, XP28482193.
International Search Report for PCT International Application No. PCT/US2016/032986, mailed on Sep. 2, 2016, 5 pages.

* cited by examiner

ADDITIVE MANUFACTURING PROCESS FOR PRODUCING CERAMIC ARTICLES USING A SOL CONTAINING NANO-SIZED PARTICLES

FIELD OF THE INVENTION

The invention relates to an additive manufacturing process for producing ceramic articles using a sol containing nano-sized particles as a construction material. The invention also relates to ceramic articles obtainable by such a process. The invention is particularly useful in the dental and orthodontic area for producing dental restorations and orthodontic brackets.

BACKGROUND ART

In conventional ceramic processing, e.g. slip casting, the ceramic slurries usually have to have a particle load as high as possible to obtain an intermediate body with a high green density. A high green density is desired and needed to enable the production of dense sintered ceramics.

Powder-based additive manufacturing technologies where the low packing density of the powder bed results in a highly porous 3D object, typically does not result in a high density ceramic without the addition of large amounts of pressure during heat treatment, making the realization of dense complex three dimension shapes challenging. Typically this method leads to densities of less than 95% of the theoretical density of the ceramic material.

The processing of slurries based on ceramic filled photopolymers with stereolithography has shown promise due to its ability to serve as a green body in the production of relatively dense ceramic articles with three dimensional architecture. Meanwhile, there are efforts trying to also use additive manufacturing technologies (like SLA technology), which are mainly used for processing polymers, for the production of ceramic articles.

However, a high particle load in a slurry can be disadvantageous for the rheological properties needed to process the slurry in an additive manufacturing technique.

On the other hand, reducing the particle load in the slurry will result in an article with a low green density which cannot be sintered to full density without cracks.

It was also observed that the intermediate body resulting from the additive manufacturing process is often not self-supporting.

U.S. Pat. No. 7,927,538 B2 (Moszner et al.) describes light-curing slips for the stereolithographic preparation of dental ceramics. The slip comprises a polyreactive binder, photoinitiator, surface-modified ceramic particles and a chain transfer agent. The viscosity of the slip lies in the range of 200 mPa*s to 2,000 Pa*s (23° C.).

U.S. Pat. No. 6,283,997M (Garg et al.) relates to a process for producing a ceramic composite bone implant having a porous network from a photocurable polymer with a high volume percent of ceramic composition. For producing the photocurable ceramic composition, alumina or hydroxyapatite having a particle size in the range of 0.05 to 10 µm (microns) is suggested.

U.S. Pat. No. 8,003,040 B2 (El-Siblani) relates to a process for producing a 3-dim object by solidifying layers with electromagnetic radiation of synergistic stimulation in a pattern.

US 2007/0072762 (Neil et al.) describes a method of making ceramic discharge vessels for a lamp application using stereolithography. The ceramic-resin mixture used for this method contains a photocurable acrylate resin and ceramic powders like aluminum oxide, aluminum oxynitride, yttrium aluminum garnet and aluminum nitride powders having a mean grain size in the range of d50=0.6 µm. The viscosity of the mixture is in a range of 200 to 25,000 mPa·s.

U.S. Pat. No. 6,955,776 (Feenstra) relates to a method for making a dental element by using a powder-based 3D printing technique. The powder can be used in dry form or in dispersed in form (slurry). The powder can be ceramic material or a metal. The ceramic material is preferably selected from $SiO_2$, $Al_2O_3$, $K_2O$, $Na_2O$, CaO, $Ba_2O$, $CrO_2$, $TiO_2$, BaO, $CeO_2$, $La_2O_3$, MgO, ZnO and $Li_2O$. The powder used in the example has median particle size of d50: 0.5 to 0.7 µm.

US 2003/0222366 A1 (Stangel et al.) describes a dental restoration production in which a digitized optical impression of a dental restoration site is captured using an intra-oral camera. The captured optical impression is converted into a data file suitable for computer-assisted production using stereolithography. The ceramic-containing material should have a viscosity in the range of 200 to 3.5 million centipoise (mPa*s). The mean particle size of the ceramic material should be from 0.05 to 5 µm.

U.S. Pat. No. 8,133,831 (Laubersheimer et al.) describes a slip for the preparation of dental ceramics by a hot-melt inkjet printing process. The slip contains ceramic particles, a radically polymerizable monomer and a wax. Ceramic particles based on Al2O3 or ZrO2 should have a particle size of 50 to 500 nm (nanometers).

Similarly, US2012/308837 A1 (Schlechtriemen et al.) describes a process for the generative preparation of shaped ceramic bodies by 3D inkjet printing using different kinds of ceramic slips. The viscosity of the slips is said to be above 200 mPa*s at room temperature.

US 2014/0183799 A1 (Fischer et al.) deals with light-curing ceramic slips for the stereolithographic preparation of high-strength ceramics using a slip based on a radically polymerizable binder, polymerization initiator, filler and a certain acidic monomer comprising a radically polymerizable group. For Y-TZP zirconium dioxide, a particle size in the range of 50 to 3500 nm is said to be preferred. The rheological properties of the slip are said to be in a range from 0.02 to 20,000 Pa*s (23° C.).

U.S. Pat. No. 8,329,296 B2 (Apel et al.) relates to primary particles of oxide-ceramic material having a primary particle size in the range of 10 to 1,000 nm which are coated with a chromophoric component. The particles may be provided as a suspension comprising a polyreactive binder, an organic solvent and additives. The suspension is said to have a viscosity from 200 to 2,000 Pa*s (23° C.).

WO 01/13815 A1 (Feenstra) describes a method for making a dental element by a 3-dim printing technique. As curable material preferably a nanomeric material consisting of nanomeric inorganic solid particles having polymerizable organic groups at their surface is used. After the printing process, the dental element is typically subject to a thermal post-treatment between 60 and 150° C. to complete curing. Instead thereof, or supplemental thereof, a thermal densification is accomplished wherein the dental element is heated to a temperature of at least 250° C. However, the compositions described in the references above have deficiencies.

Often, using a slurry or slip with ceramic particles greater than 50 nm in diameter is suggested. Not only are the slurry properties typically not suitable to produce highly accurate ceramic articles, but the larger particle sizes, even when closely packed, still limit the percentage of theoretical density possible, limiting the final material properties including mechanical as well as optical performance. Thus, there is a need for an improved additive manufacturing process.

There is also a need for high strength, translucent printed article, preferably a high strength, translucent printed zirconia article.

DESCRIPTION OF THE INVENTION

It is an object of the invention to improve existing additive manufacturing processes. In particular, it is an object of the invention to provide a process allowing the production of ceramic articles with a density close to theoretical density, high strength, high accuracy and/or good translucency.

In particular, an additive manufacturing process is desirable allowing the production of ceramic articles with good surface quality.

This object can be achieved by a process as described in the text below.

Such a process comprises the steps of:
providing a printing sol, the printing sol comprising solvent, nano-sized particles, radiation curable component(s) and photoinitiator, the printing sol having a viscosity below 500 or below 200 mPa*s (23° C.),
processing the printing sol as construction material in an additive manufacturing process to obtain a 3-dim article being in a gel state, the 3-dim article having a Volume A,
transferring the 3-dim article being in a gel state to a 3-dim article being in a dry state, preferably an aerogel or xerogel,
applying a heat treatment step to obtain a sintered 3-dim ceramic article, the ceramic article having a Volume F,
Volume A of the 3-dim article in a gel state being more than 200% or more than 300% or more than 400% or more than 500% of Volume F of the ceramic article in its sintered state.

The invention is also directed to a ceramic article obtainable or obtained according to a process as described in the present text, the ceramic article being characterized by at least one, more or all of the following features:
density: more than 98.5% with respect to theoretical density;
translucency: more than 30% determined on a polished sample having a thickness of 1 mm;
biaxial flexural strength: at least 450 MPa according to ISO 6872;
dimension in either x, y or z direction: at least 0.25 mm.

Definitions

"Ceramic" or "ceramic article" means a non-metallic material that is produced by application of heat. Ceramics are usually hard, and brittle and, in contrast to glasses or glass-ceramics, display an essentially purely crystalline structure. Ceramics are usually classified as inorganic materials.

"Crystalline" means a solid composed of atoms arranged in a pattern periodic in three dimensions (i.e., has long-range crystal structure which may be determined by techniques such as X-ray diffraction).

A "crystallite" means a crystalline domain of a solid having a defined crystal structure. A crystallite can only have one crystal phase.

"Additive manufacturing" means processes used to make 3-dimensional articles. An example of an additive manufacturing technique is stereolithography (SLA) in which successive layers of material are laid down under computer control. The articles can be of almost any shape or geometry and are produced from a 3-dimensional model or other electronic data source.

The term "dental or orthodontic ceramic article" means any ceramic article which is to be used in the dental or orthodontic field, especially for producing a dental restoration, orthodontic devices, a tooth model and parts thereof.

Examples of dental articles include crowns, bridges, inlays, onlays, veneers, facings, copings, crown and bridged framework, implants, abutments, dental milling blocks, monolithic dental restorations and parts thereof.

Examples of orthodontic articles include brackets, buccal tubes, cleats and buttons and parts thereof.

A dental or orthodontic article should not contain components which are detrimental to the patient's health and thus free of hazardous and toxic components being able to migrate out of the dental or orthodontic article. The surface of a tooth is considered not to be a dental or orthodontic article.

"Zirconia article" shall mean a 3-dimensional (3-dim) article wherein at least one of the x, y, z dimensions is at least 1 mm, at least 0.5 mm, or at least 0.25 mm, the article being comprised of at least about 80 or at least about 85 or at least about 90 or at least about 95 wt.-% zirconia.

"Monolithic dental restoration" shall mean a dental ceramic article onto the surface of which no facing or veneer has been attached. That is, the monolithic dental restoration is essentially comprised out of only one material composition. However, if desired a thin glazing layer can be applied.

"Glass" means an inorganic non-metallic amorphous material which is thermodynamically an under-cooled and frozen melt. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former. The material or article described in the present text does not contain a glass.

"Glass-ceramic" means an inorganic non-metallic material where one or more crystalline phases are surrounded by a glassy phase so that the material comprises a glass material and a ceramic material in a combination or mixture. Thus, a glass-ceramic is a material sharing many properties with both glass and more traditional crystalline ceramics. It is formed as a glass, and then made to crystallize partly by heat treatment. Glass-ceramics may refer to a mixture of lithium-, silicon- and aluminum oxides.

The material or article described in the present text does not contain a glass-ceramic.

"Sol" refers to a continuous liquid phase containing discrete particles having sizes in a range from 1 nm to 100 nm or from 1 nm to 50 nm, a so called "colloidal solution". The sols described in the present text are translucent and do show a so-called "Tyndall effect" or "Tyndall scattering". The size of the particles is below the wavelength of the visible light (400 to 750 nm).

A transparent material lets light pass through according to Snell's law (classical law of refraction). So, a picture can be seen in its details through a platelet of a transparent material.

A translucent material lets light partially permeate through although it is not fully transparent, i.e. showing a significant volume scattering of the transmitted light. The reciprocal property of translucency is opacity (O). O=1/T=I/ I0 (T=Transmission, I=Intensity of permeated light, I=Intensity of light before permeation). So, opacity values less than about 0.9 for a 1 mm thick platelet with a diameter of 15 mm are regarded as translucent (e.g. for a measurement with a Color i7 device, X-Rite corporation USA, measurement mode: remission contrast ratio). Opacity can be measured by various means: in transmission, in remission, and in remission using the contrast ratio method.

By "machining" is meant milling, grinding, cutting, carving, or shaping a material by a machine. Milling is usually faster and more cost effective than grinding. A "machinable article" is an article having a 3-dimensional shape and having sufficient strength to be machined.

A "powder" means a dry, bulk material composed of a large number of fine particles that may flow freely when shaken or tilted.

A "particle" means a substance being a solid having a shape which can be geometrically determined. The shape can be regular or irregular. Particles can typically be analysed with respect to e.g. particle size and particle size distribution. A particle can comprise one or more crystallites. Thus, a particle can comprise one or more crystal phases.

The term "associated" refers to a grouping of two or more primary particles that are aggregated and/or agglomerated. Similarly, the term "non-associated" refers to two or more primary particles that are free or substantially free from aggregation and/or agglomeration.

The term "aggregation" refers to a strong association of two or more primary particles. For example, the primary particles may be chemically bound to one another. The breakdown of aggregates into smaller particles (e.g., primary particles) is generally difficult to achieve.

The term "agglomeration" refers to a weak association of two or more primary particles. For example, particles may be held together by charge or polarity. The breakdown of agglomerates into smaller particles (e.g., primary particles) is less difficult than the breakdown of aggregates into smaller particles.

The term "primary particle size" refers to the size of a non-associated single crystal zirconia particle, which is considered to be a primary particle. X-ray diffraction (XRD) is typically used to measure the primary particle size.

"Soluble" means that a component (e.g. solid) can be completely dissolved within a solvent. That is, the substance is able to form individual molecules (like glucose) or ions (like sodium chloride) or non-settling particles (like a sol) when dispersed in water at 23° C. The solubilisation process, however, might take some time, e.g. stirring the component over a couple of hours (e.g. 10 or 20 h) might be required.

"Density" means the ratio of mass to volume of an object. The unit of density is typically g/cm$^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of a material sample can be calculated from the mass of the sample and the density of the used material. The total volume of cells in the sample is assumed to be the remainder of the sample volume (100% minus the total volume of material).

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured on different material samples (e.g. using a mercury "Poremaster 60-GT" from Quantachrome Inc., USA) according to DIN 66133. A material having an open-celled or open-porous structure can be passed through by e.g. gases.

The "average connected pore diameter" means the average size of the open-celled pores of a material. The average connected pore diameter can be calculated as described in the Examples section.

The term "calcining" or "debindering" refers to a process of heating solid material to drive off at least 90 percent by weight of volatile chemically bond components (e.g., organic components) (vs., for example, drying, in which physically bonded water is driven off by heating). Calcining is done at a temperature below a temperature needed to conduct a pre-sintering step.

The terms "sintering" or "firing" are used interchangeably. A pre-sintered ceramic article shrinks during a sintering step, that is, if an adequate temperature is applied. The sintering temperature to be applied depends on the ceramic material chosen. For $ZrO_2$ based ceramics a typical sintering temperature range is about 1100° C. to about 1550° C. Sintering typically includes the densification of a porous material to a less porous material (or a material having less cells) having a higher density, in some cases sintering may also include changes of the material phase composition (for example, a partial conversion of an amorphous phase toward a crystalline phase).

"Diafiltration" is a technique that uses ultrafiltration membranes to completely remove, replace, or lower the concentration of salts or solvents from solutions containing organic molecules. The process selectively utilizes permeable (porous) membrane filters to separate the components of solutions and suspensions based on their molecular size.

"Green body gel" means a three-dim gel resulting from the curing reaction of polymerizable components contained in a sol, including organic binder and solvent.

"Aerogel" means a three-dimensional low-density (e.g., less than 20% of theoretical density) solid. An aerogel is a porous material derived from a gel, in which the liquid component of the gel has been replaced with a gas. The solvent removal is often done under supercritical conditions. During this process the network does not substantially shrink and a highly porous, low-density material can be obtained.

"Xerogel" refers to a three-dimensional solid derived from a green body gel, in which the liquid component of the gel has been removed by evaporation under ambient conditions or at an elevated temperature.

A "green body" means an un-sintered ceramic item, typically having an organic binder present.

A "white body" means a pre-sintered ceramic item.

A "geometrically defined article" means an article the shape of which can be described with geometrical terms including 2-dimensional terms like circle, square, rectangle, and 3-dimensional terms like layer, cube, cuboid, sphere.

"Isotropic linear sintering behaviour" means that the sintering of a porous body during the sintering process occurs essentially invariant with respect to the directions x, y and z.

"Essentially invariant" means that the difference in sintering behaviour with respect to the directions x, y and z is in a range of not more than about +/−5% or +/−2% or +/−1%.

A material or composition is "essentially or substantially free of" a certain component within the meaning of the invention, if the material or composition does not contain said component as an essential feature. Thus, said component is not willfully added to the composition or material either as such or in combination with other components or ingredient of other components. A composition or material being essentially free of a certain component usually contains the component in an amount of less than about 1 wt.-% or less than about 0.1 wt.-% or less than about 0.01 wt.-% (or less than about 0.05 mol/l solvent or less than about 0.005 mol/l solvent or less than about 0.0005 mol/l solvent) with respect to the whole composition or material. Ideally the composition or material does not contain the said component at all. However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.). Unless otherwise indicated, all numbers expressing quantities of ingredients, measurement of physical properties such as described below and so forth used in the specification and claims are to be understood as being modified in all instances by the term "about".

The term "comprise" shall include also the terms "consist essentially of" and "consists of".

DETAILED DESCRIPTION OF THE INVENTION

Figure 1A:
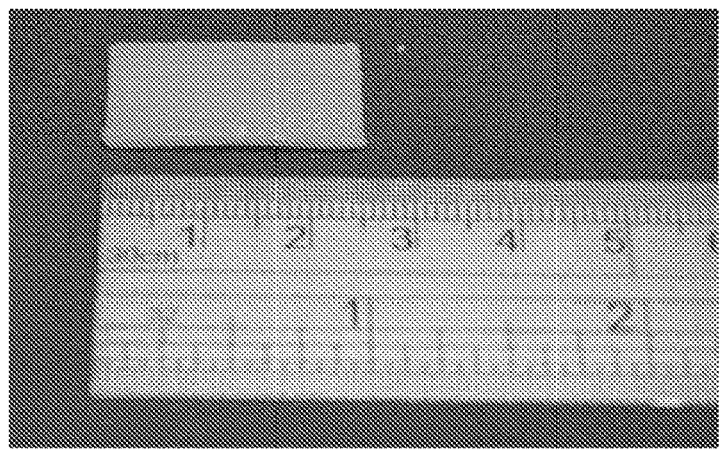
FIG. 1A to 1D show the development of shrinkage from a printed sample to the final ceramic article after sintering.

It was found that the process described in the present text is in particular useful for producing ceramic articles with a high surface accuracy.

Processing the sol to obtain a 3-dim article with a volume being much larger than the volume of the ceramic article after sintering facilitates the production of ceramic articles with high accuracy and surface smoothness.

The larger the enlargement factor for producing the 3-dim article in a gel state is, the smaller the surface defects on the ceramic article after sintering will be.

Visible surface defects which may occur during the additive manufacturing process and which may be caused by limited resolution of the manufacturing equipment, will shrink during the sintering process by the enlargement factor chosen.

However, the enlargement factor cannot be chosen freely as the 3-dim article obtained after the additive manufacturing process needs to be free-standing. That is, the 3-dim article needs to have a sufficient consistency and stability allowing it to be removed from the additive manufacturing equipment without distortion or destruction.

It was found that the sol described in the present text facilitates the production of 3-dim articles in a gel state by applying additive manufacturing techniques, wherein the 3-dim articles can be sintered to ceramic articles without cracks afterwards.

The printing sol typically contains a sufficient high amount of nano-sized particles to produce a free-standing 3-dim article in a gel state, even if the dimension of the 3-dim article in the gel state is enlarged by at least 50% or more compared to the final ceramic article in its sintered state.

On the other hand, the content of nano-sized particles is sufficiently low to produce a 3-dim article in its gel state which can be sintered afterwards without cracks. The amount of nano-sized particles being present in the sol is related to its viscosity.

Increasing the volume content of the nano-sized particles would facilitate the production of an enlarged free-standing 3-dim article in its gel state. However, such a 3-dim article cannot be sintered to its desired size and shape without cracks. The content of the nano-sized particles will be too high.

If on the other hand, the content of the nano-sized particles is too low, producing an enlarged free-standing 3-dim article in its gel state will not be possible.

It was found that a sol as described in the present text is highly suitable as construction material for producing ceramic articles according to the process described in the present text.

Compared with a subtractive processing technique, the application of an additive manufacturing technique in addition provides for a significant reduction in material usage and potentially a significant reduction in burnout and/or sintering time due to the smaller part size.

Once sintered, the ceramic articles show good physical properties like high bending strength and/or fraction resistance.

Further, the ceramic articles are sufficient translucent and can thus be used in particular in the dental and orthodontic field.

The ceramic articles can be produced with high accuracy in particular as regards details or smoothness of the surface.

During the additive manufacturing process there is no need to apply heat in order to make the construction material sufficient fluidly in order to process them through nozzles.

There is also no need to add further additives like waxes to the construction material needed for stabilizing the 3-dim article obtained after conducting the additive manufacturing technique.

The invention facilitates an additive, mould-free approach to final part fabrication as compared to existing moulding and/or subtractive processes, e.g. machining a ceramic article out of a mill blank.

By manufacturing the intermediate body in an enlarged stage may also allow for an enhanced processing speed as the requirement for a high surface resolution during the manufacturing process is reduced. Surface defects will disappear or be minimized during the shrinking process occurring during the sintering step.

Furthermore, another positive aspect of the use of a sol-gel based process with high shrinkage factors is, that it allows to finish functional surfaces or features by a subtractive process (e.g. milling etc.) or a finishing process (e.g. polishing, etc.) in the enlarged gel state to leverage the shrinkage effect for very precise details and smooth surfaces. This could additionally be feasible for increased mechanical properties (reduction of surface flaws).

The process described in the present test allows the production of sol-gel bodies with a resolution of 25 μm in z-direction and 40 μm×40 μm in x-y direction (=pixelsize) resulting in a ceramic body (after sintering) with a resolution of e.g. 12.5 μm in z-direction and 20×20 μm in x-y direction.

The invention is now described in further details:

According to the process described in the present text, a printing sol comprising nano-sized particles is provided.

The printing sol is processed as construction material in an additive manufacturing process.

The processing of the printing sol results in a 3-dim article being in a gel state. This 3-dim article has a Volume A.

The 3-dim article is transferred into a 3-dim article being in a dry state, preferably in an aerogel or xerogel state.

The 3-dim article being in a dry state is heat treated to obtain a sintered 3-dim article having a Volume F.

During the heat treatment the 3-dim article undergoes a volume shrinkage of more than 50% or more than 200% or more than 300% or more than 400% or more than 500%.

Additive manufacturing techniques which can be used include stereolithographic printing.

According to another embodiment, the process comprises the following steps:

(a) providing a printing sol comprising nano-sized particles, solvent, radiation curable monomer(s), photoinitiator, optionally organic dye(s) and optionally inhibitor(s), as described in the present text,
(b) processing the printing sol as construction material in an additive manufacturing process to obtain a 3-dim article being in a gel state, the 3-dim article having a Volume A,
(c) additive manufacturing the desired geometries by light curing,
(d) optionally cleaning the surface of the 3-dim article being in a gel state, in particular for the purpose of removing residues of non-reacted sol,
(e) optionally postcuring (e.g. by heating or lightcuring) the 3-dim article being in a gel state to a temperature in the range of 35 to 80° C. or by additional light curing, in particular for the purpose of increasing the stability of the 3-dim article being in a gel state, that 3-dim article having a Volume B,
(f) optionally soaking the 3-dim article being in a gel state with another solvent (e.g. diethylene glycol ethyl ether or ethanol),
(g) transferring the 3-dim article being in a gel state to a 3-dim article being in a dry state, preferably by applying a supercritical drying step to the 3-dim article being in a gel state, in particular for the purpose of removing the solvent, that 3-dim article having a Volume C,
(h) optionally heating the 3-dim article being in a dry state to a temperature in the range of 400 to 800° C., in particular for the purpose of removing residual organic components and to further increasing the stability, to obtain a green body, that 3-dim article having a Volume D,
(i) optionally heating the 3-dim article of the previous step to a temperature in the range of 800 to 1100° C., in particular for the purpose of creating a pre-sintered body or white body having a porous structure, that 3-dim article having a Volume E,
(j) optionally coloring at least parts of the surface of the 3-dim article of the previous step, in particular for the purpose of adjusting the color and individualizing the desired 3-d article,
(k) applying a heat treatment step to obtain a sintered 3-dim ceramic article, the ceramic article having a Volume F, wherein Volume A=or >Volume B>Volume C>Volume D>Volume E>Volume F.

The symbol "=" means that Volume A is essentially equal to Volume B. Thus, a slight deviation of e.g. +/−5% is allowed.

If desired and if a printing sol is used which already contains coloring components, steps (h), (i), (j) and (k) can be combined.

Similarly, if no coloring is desired, step (j) can be omitted and steps (h), (i) and (k) can be done within one step. Thus, there is no need or requirement to conduct those steps separately.

By continuously heating the 3-dim article being in an aerogel state to a temperature up to 1000 or 1050 or 1100° C., the organic residues will be burnt out first before the remaining inorganic components begin to adhere together and form a pre-sintered article.

According to one embodiment, the relationship of the individual volumes is as follows, for Volume A being scaled to 100:

Volume A=100
Volume B=100 to 99 or 100 to 99.5 or 100 to 99.9
Volume C=90 to 50
Volume D=70 to 25 or
Volume E=35 to 15
Volume F=25 to 2.

That is, compared to the 3-dim article being in a gel state, the 3-dim article in an aerogel state typically shows volume shrinkage in the range of 0 to 50%.

Compared to the 3-dim article being in a gel state, the 3-dim article in a pre-sintered state typically shows volume shrinkage in the range of 25 to 75%.

Compared to the 3-dim article being in a gel state, the 3-dim article in a sintered state typically shows volume shrinkage in the range of 75 to 98%.

According to one embodiment, the relationship of the individual volumes is as follows, for Volume F being scaled to 100:

Volume A (gel body)=850 to 1250 or 900 to 1100.
Volume B=850 to 1250 or 900 to 1100.
Volume C (aerogel body)=600 to 900 or 650 to 850
Volume D=250 to 700 or 300 to 600
Volume E (pre-sintered)=140 to 360 or 150 to 250
Volume F (fully sintered)=100.

According to one embodiment, Volume A of the 3-dim article being in a gel state is more than 200% or more than 300% or more than 500% or more than 800% or more than 900% of Volume F of the ceramic article being in its sintered state.

Processing the Sol

The printing sol described in the present text is processed in an additive manufacturing process, in particular in a stereolithography process (SLA).

According to one embodiment, in the process of producing a ceramic article as described in the present text, the processing step comprises the steps of providing a layer of the construction material on a surface,
radiation curing those parts of the layer of construction material which will belong to the 3-dim article to be produced,
providing an additional layer of the construction material in contact with the radiation cured surface of the previous layer,
repeating the previous steps until a 3-dim article is obtained.

Such a process comprises the step of applying radiation to the surface of a radiation curable material, wherein the radiation is applied only to those parts of the surface which will later form a part of the article to be produced.

Radiation can be applied by using e.g. a laser beam or by mask-image projection. Using a mask-image projection based stereolithographie process (MIP-SL) is sometimes preferred, as it allows a more rapid manufacturing of the article.

A MIP-SL process can be described as follows:
i. A three-dimensional digital model of the article to be produced is provided.
ii. The three-dimensional digital model is sliced by a set of horizontal planes.
iii. Each thin slice is converted into a two-dimensional mask image.
iv. The mask image is then projected with the aid of a radiation source onto the surface of the radiation curable material being located in a building platform (e.g. having the shape of a vat).
v. The radiation curable material is only cured in those regions which are exposed.
vi. The building platform containing the radiation curable material or the layer of cured material is moved relative to the radiation source, wherein a new layer of radiation curable material is provided being in contact with the layer of the cured material produced in the previous step.
vii. Steps (iv) to (vi) are repeated until the desired article is formed.

Projecting the mask image on the radiation curable material can be done either top-down or bottom-up with respect to the orientation of the vat.

Using the bottom-up technique can be beneficial as less radiation curable material is needed.

Figure 3:
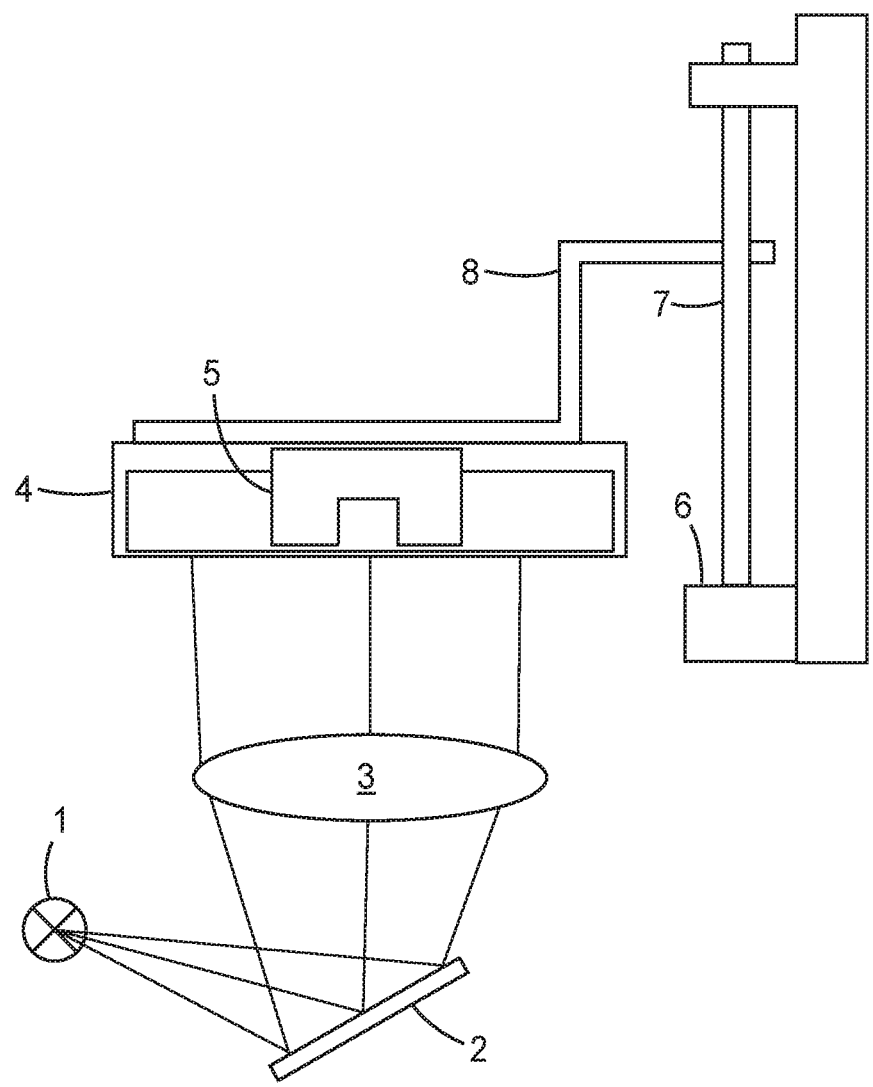
FIG. 3 schematically shows a device for conducting a stereolithography process (SLA) using the bottom-up projection technique.

In this process, the radiation cured layer is formed on the bottom of the vat, which is transparent. FIG. 3 schematically shows how such a bottom-up technique works. (1) is the light source, (2) is a mirror, (3) is a lens, (4) is the building platform having the shape of a vat, (5) is the radiation-curable construction material being located in the building platform, (6) is a motor connected with a leadscrew (7). Attached to the leadscrew (7) is a holder (8). Holder (8) is used for holding the 3-dim article to be produced.

It was found that the printing sol described in the present text is in particular useful for processing it in a mask-image projection stereolithography process using the bottom-up projection technique.

Further details of such a processing step are described in U.S. Pat. No. 4,575,330 (Hull), U.S. Pat. No. 6,283,997 (Garg et al.) or U.S. Pat. No. 8,003,040 B2 (El-Siblani). The content of these documents is herewith incorporated by reference.

The processing of the printing sol can be done by using or applying at least one or more of the following parameters:
Slice thickness of printing sol exposed to radiation: 0.001 to 0.500 mm or 0.01 to 0.4 mm;
Energy dose per layer in the range of 5 $mJ/cm^2$ to 100 $mJ/cm^2$ or 8 $mJ/cm^2$ to 50 $mJ/cm^2$.

The printing sol containing the nano-sized particles is solidified by gelation.

Preferably, the gelation process allows green body gels to be formed of any shape without cracks and green body gels that can be further processed without inducing cracks. For example, preferably, the gelation process leads to a green body gel having a structure that will not collapse when the solvent is removed; so-called "free-standing gel". The green body gel structure is compatible with and stable in a variety of solvents and conditions that may be necessary for supercritical extraction. Furthermore, the gel structure should be compatible with supercritical extraction fluids (e.g., supercritical $CO_2$). In other words, the gels should be stable and strong enough to withstand drying, so as to produce stable aerogels and give materials that can be heated to burn out the organics, pre-sintered, and densified without inducing cracks. Preferably, the resulting aerogels have relatively small and uniform pore sizes to aid in sintering them to high density at low sintering temperatures. However, preferably the pores of the aerogels are large enough to allow product gases of organic burnout to escape without leading to cracking of the aerogel. It is believed that the rapid nature of the gelation step results in an essentially homogeneous distribution of the zirconia-based particles throughout the gel, which can aid in the subsequent processing steps such as supercritical extraction, organic burnout, and sintering. It is preferable that the gel contain the minimum amount of organic material or polymer modifiers.

After processing the printing sol to form a green body gel, the 3-dim article in its gel-state is typically removed from the device used for conducting the additive manufacturing process.

If desired, the surface of the 3-dim article in its gel-state is cleaned, e.g. by rinsing the 3-dim article with a solvent or soaking in a solvent.

Suitable solvents preferably include mixtures thereof or the same solvent(s) used in the sol described in the present text.

Suitable solvents include either low boiling alcohols as described in the present text (e.g. an alcohol having a boiling point below 100° C.; like methanol, ethanol, propanol) and mixtures thereof or high boiling solvents as described in the present text, preferably the same solvent(s) being present in the sol, e.g. diethylene glycol ethyl ether.

If desired, the 3-dim article in its gel-state can be post-cured by applying radiation or heat.

Such a step may help to improve the stability of the 3-dim article in its gel-state by further increasing the degree of polymerization.

If applied, the post-curing step can be characterized by at least one, or all of the following features:
Applying radiation with wavelength from 200 to 500 or from 350 to 450 nm;
Applying a heating step with a temperature below the temperature at which drying will occur or which is used for debindering or calcining; e.g. from 30 to 110 or from 40 to 80° C.

The process of producing the ceramic article described in the present text typically also comprises a drying step to remove any organic solvents or water that may be present, transferring the 3-dim article being in a gel state to a 3-dim article being in a dry state. This can be referred to as drying the green gel body or the printed gel article regardless of the method used to remove the organic solvent.

In some embodiments, removal of the organic solvent occurs by drying the printed gel article at room temperature (e.g., 20° C. to 25° C.) or at an elevated temperature. Any desired drying temperature up to 200° C. can be used. If the drying temperature is higher, the rate of organic solvent removal may be too rapid and cracking can result. A xerogel results from this process of organic solvent removal.

Forming a xerogel can be used for drying printed gel articles with any dimensions, but is most frequently used for the preparation of relatively small sintered articles. As the gel composition dries, either at room temperature or at elevated temperatures, the density of the structure increases.

Capillary forces pull the structure together resulting in some linear shrinkage such as up to about 30%, up to 25% or up to 20%. The shrinkage is typically dependent on the amount of inorganic oxide present and the overall composition. The linear shrinkage is often in a range of 5 to 30%, 10 to 25%, or 5 to 15%. Because the drying typically occurs most rapidly at the outer surfaces, density gradients are often established throughout the structure. Density gradients can lead to the formation of cracks. The likelihood of crack formation increases with the size and the complexity of the printed gel article and with the complexity of the structure. In some embodiments, xerogels are used to prepare sintered bodies having a longest dimension no greater than about 1 centimeter.

In some embodiments, the xerogels contain some residual organic solvent. The residual solvent can be up to 6 wt.-% based on the total weight of the xerogel. For example, the xerogel can contain up to 5 wt.-%, up to 4 wt.-%, up to 3 wt.-%, up to 2 wt.-%, or up to 1 wt.-% organic solvent.

If the printed gel article has fine features that can be easily broken or cracked, it is often preferable to form an aerogel intermediate rather than a xerogel. A printed gel article of any size and complexity can be dried to an aerogel. An aerogel can be formed by drying the printed gel article, preferably under supercritical conditions. There is no capillary effect for this type of drying, and the linear shrinkage is often in a range of 0 to 25%, 0 to 20%, 0 to 15%, 5 to 15%, or 0 to 10%. The density typically remains uniform throughout the structure.

If applied, the supercritical drying step can be characterized by at least one, more or all of the following features:
a) Temperature: 20 to 100° C. or 30 to 80° C. or 15 to 150° C.;
b) Pressure: 5 to 200 MPa or 10 to 100 MPa or 1 to 20 MPa or 5 to 15 MPa;
c) Duration: 2 to 175 h or 5 to 25 h or 1 to 5 h;
d) Extraction or drying medium: carbon dioxide in its supercritical stage, A combination of features (a), (b) and (d) is sometimes preferred.

Supercritical extraction can remove all or most of the organic solvent in the printed gel article. In some embodiments, the aerogels contain some residual organic solvent. The residual solvent can be up to 6 wt.-% based on the total weight of the aerogel. For example, the aerogel can contain up to 5 wt.-%, up to 4 wt.-%, up to 3 wt.-%, up to 2 wt.-%, or up to 1 wt.-% organic solvent.

The removal of organic solvent results in the formation of pores within the dried structure. Preferably, the pores are sufficiently large to allow gases from the decomposition products of the polymeric material to escape without cracking the structure when the dried structure is further heated to burnout the organic material and to form a sintered article.

The article obtained after having conducted the supercritical drying step can typically be characterized by at least one or more of the following properties:
showing a $N_2$ adsorption and/or desorption isotherm with a hysteresis loop;
showing a $N_2$ adsorption and desorption of isotherm type IV according to IUPAC classification and a hysteresis loop;
showing a $N_2$ adsorption and desorption isotherm of type IV with a hysteresis loop of type H1 according to IUPAC classification;
showing a $N_2$ adsorption and desorption isotherm of type IV with a hysteresis loop of type H1 according to IUPAC classification in a p/p0 range of 0.70 to 0.99;
BET surface: from 120 to 200 m²/g or from 130 to 190 m²/g.

A heating step is conducted to remove organic residues being still present in the 3-dim article before final sintering. Removing organic residues before sintering reduces the risks of cracks during sintering.

Such a heating step is sometimes also referred to as debindering or calcining step. As a result a so-called "white body" is obtained.

The heating step is typically conducted at a temperature below 800° C. or below 700 or below 600° C. A typical temperature range is from 400 to 800° C. or from 500 to 700° C.

The heating step is typically conducted for a time needed to combust the organic components in the 3-dim article.

A typical time frame is from 5 to 100 h or from 10 to 50 h.

The heating is typically conducted at ambient conditions (i.e. ambient air, ambient pressure).

The body obtained after a debindering or calcining step can be further treated with heat to obtain a pre-sintered article.

Such a pre-sintered article is porous and can be colored using commercially available coloring liquids. If either no coloring is desired or if the article is already colored, a pre-sintering step can be omitted.

The pre-sintered article can typically be characterized by the following properties:
showing a $N_2$ adsorption and/or desorption isotherm with a hysteresis loop;
showing a $N_2$ adsorption and desorption of isotherm type IV according to IUPAC classification and a hysteresis loop;
showing a $N_2$ adsorption and desorption isotherm of type IV with a hysteresis loop of type H1 according to IUPAC classification;
showing a $N_2$ adsorption and desorption isotherm of type IV with a hysteresis loop of type H1 according to IUPAC classification in a p/p0 range of 0.70 to 0.99;
BET surface: from 15 to 100 m²/g or from 16 to 60 m²/g.

The conditions to be applied for conducting a pre-sintering step can be described as follows:
temperature: from 800 to 1100° C. or from 950 to 1090° C. or from 975 to 1080° C.;
atmosphere: air or inert gas (e.g. nitrogen, argon);
duration: until a density of 40 to 60% of the final density of the material has been reached.

If desired, the pre-sintered article optionally can be soaked in a basic solution such as an aqueous solution of ammonium hydroxide. Soaking can be effective to remove undesirable ionic species such as sulfate ions because of the porous nature of the articles at this stage of the process. Sulfate ions can ion exchange with hydroxyl ions. If sulfate ions are not removed, they can generate small pores in the sintered articles that tend to reduce the translucency and/or the strength.

More specifically, the ion exchange process often includes soaking the article that has been heated to remove organic material in an aqueous solution of 1 N ammonium hydroxide. This soaking step is often for at least 8 h, at least 16 h, or at least 24 h. After soaking, the article is removed from the ammonium hydroxide solution and washed thoroughly with water. The article can be soaked in water for any desired period of time such as at least 30 min, at least 1 h, at least 2 h, or at least 4 h. The soaking in water can be repeated several times, if desired, by replacing the water with fresh water.

After soaking, the article is typically dried in an oven to remove the water. For example, the article can be dried by heating in an oven set at a temperature equal to at least 80° C., at least 90° C., or at least 100° C. For example, the temperature can be in a range of 80° C. to 150° C., 90° C. to 150° C., or 90° C. to 125° C. for at least 30 min, at least 60 min, or at least 120 min.

If desired, at least parts of the surface of the 3-dim article being in an absorbent stage can be coloured. Colouring can be effected by using colouring solutions.

A suitable colouring solution typically contains a solvent and certain ions.

The solvent is able to dissolve the ion(s) contained in the treatment solution. If desired, mixtures of different solvents can be used.

Suitable solvents include water, alcohols (especially low-boiling alcohols, e.g. with a boiling point below about 100° C.) and ketones. Specific examples of solvents which can be used for dissolving the cations of the non-colouring agent include water, methanol, ethanol, iso-propanol, n-propanol, butanol, acetone, and mixtures thereof.

The solvent is typically present in an amount from 50 to 99.9 wt.-% or from 60 to 99 wt.-% or from 75 to 95 wt.-%, wt.-% with respect to the whole colouring solution.

The colouring solution has typically an adequate viscosity so that a sufficient amount of solution can not only be applied to the surface of the porous zirconia article but also is able to migrate into the pores of the zirconia article.

Adjusting the viscosity to a value as indicated above can be beneficial in that the solution can be more accurately applied to particular sections or regions of the porous dental zirconia article obtained after presintering the printed ceramic article.

If the viscosity of the colouring solution is too high, the colouring solution might not be able to sufficiently enter the pores of the zirconia material. On the other hand, if the viscosity of the colouring solution is too low, the colouring solution might migrate into the pores too rapidly and might diffuse into the whole article.

According to one embodiment, the colouring solution comprises coloring ions selected from ions of Fe, Mn, Er, Pr, Tb, V, Cr, Co, Mo and mixtures thereof. These ions were found to be particularly useful for use in the dental or orthodontic field.

The solution may also contain phase stabilizers including ions of Y, Ce, Mg, Ca, rare earth elements and mixtures thereof. The addition of phase stabilizers may further facilitate the stabilization of a certain crystalline phase (e.g. cubic or tetragonal phase) of the zirconia components present in the ceramic article.

The solution may also contain on or more complexing agent(s). The complexing agent(s) may support the penetration of the coloring solution.

The colouring solution can be applied to the surface of the 3-dim article with the help of application devices including brushes, sponges, (hollow) needles, pens, mixing appliances and combinations thereof.

However, the colouring ions can also be added to the sol for use in the additive manufacturing process as described in the present text. In this case, the obtained article is already coloured.

A sintering step is finally carried out to obtain a ceramic article having a density of at least 99 or at least 99.5 or at least 99.9% of the theoretical density.

Sintering of the 3-dim article is typically carried out under the flowing conditions:

temperature: from 1150 to 1500° C. or from 1200 to 1400° C. or from 1250 to 1350° C. or from 1200 to 1400° or from above 1300 to 1400° C. or above 1320° C. to 1400° C. or above 1340° C. or above 1350° C.;
atmosphere: air or inert gas (e.g. nitrogen, argon);
pressure: ambient pressure (e.g. 1013 mbar);
duration: until a density of about 99 to about 100% of the final density of the material has been reached.

Properties of the sintered ceramic article are described in the present text further down below.

The preparation of the printing sol used in the additive manufacturing process typically starts with the preparation of a starting sol.

A precursor solution is prepared by combining a zirconium salt (e.g. acetate) solution and a solvent (e.g. water). A phase stabilizing agent (e.g. yttrium acetate) is added and dissolved in the precursor solution. The resulting composition is pumped e.g. through a hydrothermal reactor.

Suitable hydrothermal reactors are described e.g. in U.S. Pat. No. 5,453,262 (Dawson et al.) and U.S. Pat. No. 5,652,192 (Matson et al.).

The content of tetragonal and/or cubic phase of the zirconia crystallites can be adjusted by varying the amount of phase stabilizing components added during the production method.

Phase stabilizing components which can be used include Ce, Mg, Ca, Y, rare earth elements and combinations thereof.

Although any of a variety of known methods can be used to provide the zirconia-based particles, preferably they are prepared using hydrothermal technology.

In one exemplary embodiment, the zirconia-based sols are prepared by hydrothermal treatment of aqueous metal salt (e.g., a zirconium salt, an yttrium salt, and an optional lanthanide element salt or aluminum salt) solutions, suspensions or a combination of them.

The aqueous metal salts, which are selected to be soluble in water, are typically dissolved in the aqueous medium. The aqueous medium can be water or a mixture of water with other water soluble or water miscible materials. In addition, the aqueous metal salts and other water soluble or water miscible materials which may be present are typically selected to be removable during subsequent processing steps and to be non-corrosive.

At least a majority of the dissolved salts in the feedstock are usually carboxylate salts rather than halide salts, oxyhalide salts, nitrate salts, or oxynitrate salts. Although not wanting to be bound by theory, it is believed that halide and nitrate anions in the feedstock tend to result in the formation of zirconia-based particles that are predominately of a monoclinic phase rather than the more desirable tetragonal or cubic phases. Further, carboxylates and/or acids thereof tend to be more compatible with an organic matrix material compared to halides and nitrates. Although any carboxylate anion can be used, the carboxylate anion often has no greater than 4 carbon atoms (e.g., formate, acetate, propionate, butyrate, or a combination thereof). The dissolved salts are often acetate salts. The feedstock can further include, for example, the corresponding carboxylic acid of the carboxylate anion. For example, feedstocks prepared from acetate salts often contain acetic acid.

One exemplary zirconium salt is zirconium acetate salt, represented by a formula such as $ZrO_{((4-n)/2)}^{n+}(CH3COO^-)_n$, where n is in the range from 1 to 2. The zirconium ion may be present in a variety of structures depending, for example, on the pH of the feedstock. Suitable aqueous solutions of zirconium acetate are commercially available, for example, from Magnesium Elektron, Inc., Flemington, N.J., that contain, for example, up to 17 wt.-% zirconium, up to 18 wt.-% zirconium, up to 20 wt.-% zirconium, up to 22 wt.-%, up to 24 wt.-%, up to 26 wt.-%, and up to 28 wt.-% zirconium, based on the total weight of the solution.

Similarly, exemplary yttrium salts, and aluminum salts often have a carboxylate anion, and are commercially available. Because these salts are typically used at much lower concentration levels than the zirconium salt, however, salts other than carboxylate salts (e.g., acetate salts) may also be useful (e.g., nitrate salts).

The total amount of the various salts dissolved in the feedstock can be readily determined based on the total percent solids selected for the feedstock. The relative amounts of the various salts can be calculated to provide the selected composition for the zirconia-based particles.

Typically, the pH of the feedstock is acidic. For example, the pH is usually less than 6, less than 5, or even less than 4 (in some embodiments, in a range from 3 to 4).

The liquid phase of the feedstock is typically predominantly water (i.e., the liquid phase is an aqueous based medium). Preferably, the water is deionized to minimize the introduction of alkali metal ions, alkaline earth ions, or both into the feedstock. Optionally, water-miscible organic co-solvents are included in the liquid phase in amounts, for example, up 20 wt.-%, based on the weight of the liquid phase. Suitable co-solvents include 1-methoxy-2-propanol, ethanol, iso-propanol, ethylene glycol, N,N-dimethylacetamide, and N-methyl pyrrolidone.

When subjected to hydrothermal treatment, the various dissolved salts in the feedstock undergo hydrolysis and condensation reactions to form the zirconia-based particles. These reactions are often accompanied with the release of an acidic by-product. That is, the by-product is often one or more carboxylic acids corresponding to the zirconium carboxylate salt plus any other carboxylate salt in the feedstock. For example, if the salts are acetate salts, acetic acid is formed as a by-product of the hydrothermal reaction.

Any suitable hydrothermal reactor can be used for the preparation of the zirconia-based particles. The reactor can be a batch or continuous reactor. The heating times are typically shorter and the temperatures are typically higher in a continuous hydrothermal reactor compared to a batch hydrothermal reactor. The time of the hydrothermal treatments can be varied depending, for example, on the type of reactor, the temperature of the reactor, and the concentration of the feedstock. The pressure in the reactor can be autogeneous (i.e., the vapour pressure of water at the temperature of the reactor), can be hydraulic (i.e., the pressure caused by the pumping of a fluid against a restriction), or can result from the addition of an inert gas such as nitrogen or argon. Suitable batch hydrothermal reactors are available, for example, from Parr Instruments Co., Moline, Ill.

In some embodiments, the feedstock is passed through a continuous hydrothermal reactor. As used herein, the term "continuous" with reference to the hydrothermal reactor system means that the feedstock is continuously introduced and an effluent is continuously removed from the heated zone. The introduction of feedstock and the removal of the effluent typically occur at different locations of the reactor. The continuous introduction and removal can be constant or pulsed.

The dimensions of the tubular reactor can be varied and, in conjunction with the flow rate of the feedstock, can be selected to provide suitable residence times for the reactants within the tubular reactor. Any suitable length tubular reactor can be used provided that the residence time and temperature are sufficient to convert the zirconium in the feedstock to zirconia-based particles. The tubular reactor often has a length of at least 0.5 meter (in some embodiments, at least 1 m, 2 m, 5 m, 10 m, 15 m, 20 m, 30 m, 40 m, or even at least 50 m). The length of the tubular reactor in some embodiments is less than 500 m (in some embodiments, less than 400 m, 300 m, 200 m, 100 m, 80 m, 60 m, 40 m, or even less than 20 m).

Tubular reactors with a relatively small inner diameter are sometimes preferred. For example, tubular reactors having an inner diameter no greater than about 3 cm are often used because of the fast rate of heating of the feedstock that can be achieved with these reactors. Also, the temperature gradient across the tubular reactor is less for reactors with a smaller inner diameter compared to those with a larger inner diameter. The larger the inner diameter of the tubular reactor, the more this reactor resembles a batch reactor. However, if the inner diameter of the tubular reactor is too small, there is an increased likelihood of the reactor becoming plugged or partially plugged during operation resulting from deposition of material on the walls of the reactor. The inner diameter of the tubular reactor is often at least 0.1 cm (in some embodiments, at least 0.15 cm, 0.2 cm, 0.3 cm, 0.4 cm, 0.5 cm, or even at least 0.6 cm). In some embodiments, the diameter of the tubular reactor is no greater than 3 cm (in some embodiments, no greater than 2.5 cm, 2 cm, 1.5 cm, or even greater than 1 cm; in some embodiments, in a range from 0.1 to 2.5 cm, 0.2 cm to 2.5 cm, 0.3 cm to 2 cm, 0.3 cm to 1.5 cm, or even 0.3 cm to 1 cm).

In a continuous hydrothermal reactor, the temperature and the residence time are typically selected in conjunction with the tubular reactor dimensions to convert at least 90 mole percent of the zirconium in the feedstock to zirconia-based particles using a single hydrothermal treatment. That is, at least 90 mole percent of the dissolved zirconium in the feedstock is converted to zirconia-based particles within a single pass through the continuous hydrothermal reactor system.

Alternatively, for example, a multiple step hydrothermal process can be used. For example, the feedstock can be subjected to a first hydrothermal treatment to form a zirconium-containing intermediate and a by-product such as a carboxylic acid. A second feedstock can be formed by removing at least a portion of the by-product of the first hydrothermal treatment from the zirconium-containing intermediate. The second feedstock can then be subjected to a second hydrothermal treatment to form a sol containing the zirconia-based particles. Further details on this process are described, for example, in U.S. Pat. No. 7,241,437 (Davidson et al.).

If a two-step hydrothermal process is used, the percent conversion of the zirconium-containing intermediate is typically in a range from 40 to 75 mol-%. The conditions used in the first hydrothermal treatment can be adjusted to provide conversion within this range. Any suitable method can be used to remove at least part of the by-product of the first hydrothermal treatment. For example, carboxylic acids such as acetic acid can be removed by a variety of methods such as vaporization, dialysis, ion exchange, precipitation, and filtration.

When referring to a continuous hydrothermal reactor, the term "residence time" means the average length of time that the feedstock is within the heated portion of the continuous hydrothermal reactor system.

Any suitable flow rate of the feedstock through the tubular reactor can be used as long as the residence time is sufficiently long to convert the dissolved zirconium salt to zirconia-based particles. That is, the flow rate is often selected based on the residence time needed to convert the zirconium in the feedstock to zirconia-based particles. Higher flow rates are desirable for increasing throughput and for minimizing the deposition of materials on the walls of the tubular reactor. A higher flow rate can often be used when the length of the reactor is increased or when both the length and diameter of the reactor are increased. The flow through the tubular reactor can be either laminar or turbulent.

In some exemplary continuous hydrothermal reactors, the reactor temperature is in the range from 170° C. to 275° C., 170° C. to 250° C., 170° C. to 225° C., 180° C. to 225° C., 190° C. to 225° C., 200° C. to 225° C., or even 200° C. to 220° C. If the temperature is greater than about 275° C., the pressure may be unacceptably high for some hydrothermal reactors systems. However, if the temperature is less than about 170° C., the conversion of the zirconium slat in the feedstock to zirconia-based particles may be less than 90 wt.-% using typical residence times.

The effluent of the hydrothermal treatment (i.e., the product of the hydrothermal treatment) is a zirconia-based sol and can be referred to as the "sol effluent". The sol effluent is a dispersion or suspension of the zirconia-based particles in the aqueous-based medium. The sol effluent contains at least 3 wt.-% zirconia-based particles dispersed, suspended, or a combination thereof based on the weight of the sol. In some embodiments, the sol effluent contains at least 5 wt.-%, at least 6 wt.-%, at least 8 wt.-%, or at least 10 wt.-% zirconia-based particles based on the weight of the sol. The wt.-% zirconia-based particles can be up to 16 wt.-% or higher, up to 15 wt.-%, up to 12 wt.-%, or up to 10 wt.-%.

The sol effluent usually contains non-associated zirconia-based particles. The sol effluent is typically clear or slightly cloudy. In contrast, zirconia-based sols that contain agglomerated or aggregated particles usually tend to have a milky or cloudy appearance. The sol effluent often has a high optical transmission due to the small size and non-associated form of the primary zirconia particles in the sol. High optical transmission of the sol effluent can be desirable in the preparation of transparent or translucent sintered articles. As used herein, "optical transmission" refers to the amount of light that passes through a sample (e.g., a sol effluent or printing sol) divided by the total amount of light incident upon the sample. The percent optical transmission may be calculated using the equation $$100(I/Io)$$

where I is the light intensity Pa*ssing though the sample and Io is the light intensity incident on the sample.

The optical transmission through the sol effluent is often related to the optical transmission through the printing sol (reaction mixture used to form the gel body). Good transmission helps ensure that adequate curing occurs during the formation of the gel body.

The optical transmission may be determined using an ultraviolet/visible spectrophotometer set, for example, at a wavelength of 420 nm or 600 nm with a 1 cm path length. The optical transmission is a function of the amount of zirconia in a sol. For sol effluents containing about 1 wt.-% zirconia, the optical transmission is typically at least 70 percent, at least 80 percent, at least 85 percent, or at least 90 percent at either 420 nm or 600 nm. For sol effluents containing about 10 wt.-% zirconia, the optical transmission is typically at least 20 percent, at least 25 percent, at least 30 percent, at least 40 percent, at least 50 percent, or at least 70 percent at either 420 nm or 600 nm.

The zirconia-based particles in the sol effluent are crystalline and can be cubic, tetragonal, monoclinic, or a combination thereof. Because the cubic and tetragonal phases are difficult to differentiate using x-ray diffraction techniques, these two phases are typically combined for quantitative purposes and are referred to as the "cubic/tetragonal" phase. The percent cubic/tetragonal phase can be determined, for example, by measuring the peak area of the x-ray diffraction peaks for each phase and using the following equation:

$$\% \ C/T = 100(C/T) \div (C/T + M)$$

In this equation, "C/T" refers to the area of the diffraction peak for the cubic/tetragonal phase, "M" refers to the area of the diffraction peak for the monoclinic phase, and "% C/T" refers to the wt.-% cubic/tetragonal crystalline phase. The details of the x-ray diffraction measurements are described further in the Example section below.

Typically, at least 50 wt.-% of the zirconia-based particles in the sol effluent have a cubic structure, a tetragonal structure, or a combination thereof. A greater content of the cubic/tetragonal phase is usually desired. The amount of cubic/tetragonal phase is often at least 60 wt.-%, at least 70 wt.-%, at least 75 wt.-%, at least 80 wt.-%, at least 85 wt.-%, at least 90 wt.-%, or at least 95 wt.-% based on a total weight of all crystalline phases present in the zirconia-based particles.

Different sols having different yttria contents can be mixed in order to adjust the ratio of cubic to tetragonal phase content of the zirconia crystallites contained therein, if desired.

The zirconia-based particles within the sol effluent are crystalline and have an average primary particle size no greater than 50 nm, no greater than 45 nm, no greater than 40 nm, no greater than 30 nm, no greater than 20 nm, no greater than 15 nm, or no greater than 10 nm. The zirconia-based particles typically have an average primary particle size that is at least 1 nm, at least 2 nm, at least 3 nm, at least 4 nm, or at least 5 nm. In some embodiments, the average primary particle size is in a range of 5 to 50 nm, 5 to 45 nm, 2 to 40 nm, 5 to 40 nm, 2 to 25 nm, 5 to 25 nm, 2 to 20 nm, 5 to 20 nm, 2 to 15 nm, 5 to 15 nm, or 2 to 10 nm. The average primary particle size, which refers to the non-associated particle size of the zirconia particles, can be determined by x-ray diffraction as described in the Example section.

The particles in the sol effluent are typically non-associated and the average particle size is the same as the primary particle size. The extent of association between the primary particles can be determined from the volume-average particle size. The volume-average particle size can be measured using Photon Correlation Spectroscopy as described in more detail in the Examples section below. Briefly, the volume distribution (percentage of the total volume corresponding to a given size range) of the particles is measured. The volume of a particle is proportional to the third power of the diameter. The volume-average size is the size of a particle that corresponds to the mean of the volume distribution. If the zirconia-based particles are associated, the volume-average particle size provides a measure of the size of the aggregate and/or agglomerate of primary particles. If the particles of zirconia are non-associated, the volume-average particle size provides a measure of the size of the primary particles. The zirconia-based particles typically have a volume-average size of up to 100 nm. For example, the volume-average size can be up to 90 nm, up to 80 nm, up to 75 nm, up to 70 nm, up to 60 nm, up to 50 nm, up to 40 nm, up to 30 nm, up to 25 nm, up to 20 nm, or up to 15 nm, or even up to 10 nm.

A quantitative measure of the degree of association between the primary particles in the sol effluent is the dispersion index. As used herein the "dispersion index" is defined as the volume-average particle size divided by the primary particle size. The primary particle size (e.g., the weighted average crystallite size) is determined using x-ray diffraction techniques and the volume-average particle size is determined using Photon Correlation Spectroscopy. As the association between primary particles decreases, the dispersion index approaches a value of 1 but can be somewhat higher or lower. The zirconia-based particles typically have a dispersion index in a range of from 1 to 7. For example, the dispersion index is often in a range 1 to 5, 1 to 4, 1 to 3, 1 to 2.5, or even 1 to 2.

Photon Correlation Spectroscopy also can be used to calculate the Z-average primary particle size. The Z-average size is calculated from the fluctuations in the intensity of scattered light using a cumulative analysis and is proportional to the sixth power of the particle diameter. The volume-average size will typically be a smaller value than the Z-average size. The zirconia-based particles tend to have a Z-average size that is up to 100 nm. For example, the Z-average size can be up to 90 nm, up to 80 nm, up to 70 nm, up to 60 nm, up to 50 nm, up to 40 nm, up to 35 nm, up to 30 nm, up to 20 nm, or even up to 15 nm.

Depending on how the zirconia-based particles are prepared, the particles may contain at least some organic material in addition to the inorganic oxides. For example, if the particles are prepared using a hydrothermal approach, there may be some organic material attached to the surface of the zirconia-based particles. Although not wanting to be bound by theory, it is believed that organic material originates from the carboxylate species (anion, acid, or both) included in the feedstock or formed as a by-product of the hydrolysis and condensation reactions (i.e., organic material is often adsorbed on the surface of the zirconia-based particles). For example, in some embodiments, the zirconia-based particles contain up to 15 wt.-%, up to 12 wt.-%, up to 10 wt.-%, up to 8 wt.-%, or even up to 6 wt.-% organic material based on a total weight of the zirconia-based particles.

The starting sol typically contains at least 2 wt.-% zirconia-based particles dispersed, suspended, or a combination thereof in an aqueous medium. In some embodiments, the zirconia-based particles can contain (a) 0 to 10 mol-% of a lanthanide element oxide, based on total moles of inorganic oxide in the zirconia-based particles, and (b) 0 to 30 mol-% yttrium oxide, based on total moles of inorganic oxide in the zirconia-based particles. The zirconia-based particles are crystalline and have an average primary particle size no greater than 50 nm or no greater than 45 nm. In some embodiments, cerium oxide, magnesium oxide, ytterbium oxide, and/or calcium oxide may be used with or in place of the yttria.

Depending on the intended use of the final sintered articles, other inorganic oxides can be included in the zirconia-based particles in addition to zirconium oxide.

Thus, according to one embodiment, the sol described in the present text may comprise one or more inorganic colouring agent(s). The nature and structure of the inorganic colouring agent(s) is not particularly limited, either unless the desired result cannot be achieved.

In preferred embodiments the metal ion is not a free salt, but rather is incorporated into the zirconia-based particles.

Up to 30 mol-%, up to 25 mol-%, up to 20 mol-%, up to 10 mol-%, up to 5 mol-%, up to 2 mol-%, or up to 1 mol-% of the zirconia-based particles can be $Y_2O_3$, $La_2O_3$, $Al_2O_3$, $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, $NiO$, $CuO$, $V_2O_3$, $Bi_2O_3$, $Ga_2O_3$, $Lu_2O_3$, $HfO_2$, or mixtures thereof. Inorganic oxide such as $Fe_2O_3$, $MnO_2$, $Co_2O_3$, $Cr_2O_3$, $NiO$, $CuO$, $Ga_2O_3$, $Er_2O_3$, $Pr_2O_3$, $Eu_2O_3$, $Dy_2O_3$, $Sm_2O_3$, $V_2O_3$, or $W_2O_3$ may be added may be added, for example, to alter the colour of the ceramic article to be produced.

If the sol is to be used for producing dental or orthodontic articles, the following inorganic colouring agent (s) were found to be useful: ions of Mn, Fe, Cu, Pr, Nd, Sm, Eu, Tb, Dy, Er, Bi and mixtures thereof, preferably ions of Er, Tb, Mn, Bi, Nd or Fe, Pr, Co, Cr or V, Cu, Eu, Sm, Dy, with Er, Tb, Mn, Bi, Nd being sometimes particularly preferred.

If present, the inorganic colouring agent(s) is present in the following amounts:

Lower amount: at least 0.001 or at least 0.005 or at least 0.01 wt.-%;

Upper amount: at most 0.02 or at most 0.05 or at most 0.5 wt.-%;

Range: from 0.001 to 0.5 or from 0.005 to 0.05 wt.-%; calculated on the weight of the colouring ion being present in the colouring agent and with respect to the weight of the sol. The starting sol is typically concentrated.

To obtain a more concentrated sol, at least a portion of the aqueous-based medium is removed from the zirconia-based sol. Any known means for removing the aqueous-based medium can be used. This aqueous-based medium contains water and often contains dissolved carboxylic acids and/or anions thereof that are present in the feedstock or that are by-products of the reactions that occur within the hydrothermal reactor. As used herein, the term "carboxylic acids and/or anions thereof" refers to carboxylic acids, carboxylate anions of these carboxylic acids, or mixtures thereof. The removal of at least a portion of these dissolved carboxylic acids and/or anions thereof from the zirconia-based sol may be desirable in some embodiments. The zirconia-based sol can be subjected, for example, to at least one of vaporization, drying, ion exchange, solvent exchange, diafiltration, or dialysis, for example, for concentrating, removal of impurities or to compatibilize with other components present in the sol.

According to one embodiment, the zirconia based sol can be subjected to dialysis or diafiltration.

Dialysis and diafiltration both tend to remove at least a portion of the dissolved carboxylic acids and/or anions thereof. For dialysis, a sample of the effluent can be positioned within a membrane bag that is closed and then placed within a water bath. The carboxylic acid and/or carboxylate anions diffuse out of the sample within the membrane bag. That is, these species will diffuse out of the effluent through the membrane bag into the water bath to equalize the concentration within the membrane bag to the concentration in the water bath. The water in the bath is typically replaced several times to lower the concentration of species within the bag. A membrane bag is typically selected that allows diffusion of the carboxylic acids and/or anions thereof but does not allow diffusion of the zirconia-based particles out of the membrane bag.

For diafiltration, a permeable membrane is used to filter the sample. The zirconia particles can be retained by the filter if the pore size of the filter is appropriately chosen. The dissolved carboxylic acids and/or anions thereof pass through the filter. Any liquid that passes through the filter is replaced with fresh water. In a discontinuous diafiltration process, the sample is often diluted to a pre-determined volume and then concentrated back to the original volume by ultrafiltration. The dilution and concentration steps are repeated one or more times until the carboxylic acid and/or anions thereof are removed or lowered to an acceptable concentration level. In a continuous diafiltration process, which is often referred to as a constant volume diafiltration process, fresh water is added at the same rate that liquid is removed through filtration. The dissolved carboxylic acid and/or anions thereof are in the liquid that is removed.

While the majority of the yttrium and lanthanum, if present, are incorporated into the crystalline zirconia particles there is a fraction of these metals that can be removed during the diafiltration or dialysis process. The actual composition of a sol after diafiltration may be different than that before dialysis.

The content of the crystalline nano-sized zirconia particles in the concentrated starting sol is typically in a range from 20 to 70 wt.-%.

In some embodiments, the concentrated zirconia based sol can be subjected to a solvent exchange process.

An organic solvent having a higher boiling point than water can be added to the effluent. Examples of organic solvents that are suitable for use in a solvent exchange method include 1-methoxy-2-propanol, N-methyl pyrrolidone or diethylene glycol ethyl ether. The water then can be removed by a method such as distillation, rotary evaporation, or oven drying. Depending on the conditions used for removing the water, at least a portion of the dissolved carboxylic acid and/or anion thereof can also be removed. Other organic matrix material can be added to the treated effluent (i.e., other organic matrix material can be added to the zirconia-based particle suspended in the organic solvent used in the solvent exchange process).

A zirconia based sol comprises zirconia-based particles dispersed and/or suspended (i.e., dispersed, suspended, or a combination thereof) in an aqueous/organic matrix.

The sol to be used in the additive manufacturing process described in the present text (printing sol) is obtained by adding further components to the starting sol.

This can include addition of surface modifiers, addition of radiation curable monomer(s) or oligomer(s), photoinitiators, inhibitors, organic dyes, solvents and a mixture or combination thereof. The concentrations and a composition can be further adjusted through diafiltration, distillation or comparable processes, if desired.

In certain embodiments the printing sol to be used in the additive manufacturing process can be characterized by at least one or more, sometimes all of the following parameters:

a) being translucent in a wave length range from 420 to 600 nm;
b) showing a transmission of at least 5% at 420 nm determined for a path length of 10 mm;
c) substantially free of associated nano-sized zirconia particles;
d) being acidic, i.e. having a pH in the range of 1 to 6 or 2 to 5 or 2 to 4 if brought in contact with water;
e) viscosity: less than 200 or less than 180 or less than 150 or less than 100 or less than 50 or less than 20 mPa*s at 23° C.

It was found that using a translucent printing sol can be beneficial for improving the printing results or detail resolution of the surface of the ceramic article. In contrast to e.g. a slips or slurries, translucent printing sols as described in the present text show less scattering of light, which is used for polymerizing the radiation curable components contained in the sol.

The increased translucency allows for a more shallow cure gradient, which may also allow for a more uniform cure across the entire structure to be obtained, as lower energy doses are required to cure through a translucent material. Many of the compositions and slurries suggested as construction material in an additive manufacturing process described in the prior art are not translucent but rather opaque due to the larger size of the dispersed particles.

The printing sol described in the present text allows transmission of ultraviolet/visible radiation.

The percent transmission of the printing sol containing 40 wt.-% zirconia-based particles is typically at least 5% when measured at 420 nm in a 1 cm sample cell (i.e., the spectrophotometer has a 1 cm path length). In some examples, the percent transmission under these same conditions is at least 7%, at least 10% and can be up to 20% or higher, up to 15%, or up to 12%. The percent transmission of a printing sol composition containing 40 wt.-% zirconia-based particles is typically at least 20% when measured at 600 nm in a 1-centimeter sample cell. In some examples, the percent transmission under these same conditions is at least 30%, at least 40% and can be up to 80% or higher, up to 70%, or up to 60%. The printing sol is translucent and not opaque. In some embodiments, the cured green body gel compositions are translucent as well.

The transmission of the ultraviolet/visible radiation should be sufficiently high to form a gel composition layer that adheres to the previously built gel composition layer in a manner that minimizes over build for sufficient realization of the digital file input shape in the gel composition. The "slice thickness" is often slightly smaller than the depth of cure to allow for layer adhesion. Minimizing the difference between "slice thickness" and cure depth can be advantageous for enhanced resolution.

Further, filled radiation curable compositions, e.g. slurries or slips, typically result in a reduction in green body strength compared to non-filled curable compositions. Smaller non-associated particles typically provide more surface area for the two phases to interact in an SLA process. This may result in a more robust green body or green body gel.

In addition, using nanoscale particles theoretically hold the potential for printing a nanoscale layer. This would not be possible with larger particles. For example, a 25-μm layer thickness setting with a slurry that has 50 μm particles doesn't allow for fine realization of the fidelity offered with a small layer thickness. This includes not only the resolution of the material that makes up the part, but also the voids and internal structures that can be realized within the 3D printed part. This also includes the ability to realize ultrathin walls.

Similarly, sols with uniformly dispersed nanoscale particles theoretically allow for smoother surface finishes to be achieved as compared to those with larger particles.

Finally, smaller nanoparticles provide opportunity for a more uniform and higher density final sintered part, resulting in greater mechanical and optical performance of the part, important for several applications.

Using an acidic sol is also often beneficial. It was found that an acidic sol containing nano-zirconia particles is more stable than a neutral or basic sol. The risk of formation of agglomerated or aggregated particles contained therein is reduced. However, the sol should not be too acidic. If the sol is too acidic, the risk of the formation of agglomerated or aggregated particles is sometimes increased.

A printing sol having a viscosity in the above range is beneficial e.g. as it can easily be processed through thin nozzles and tubes. There is no need for heating either the nozzles or tubes of the manufacturing unit or the construction material itself.

Typically, a reaction mixture containing filler particles (e.g. a slurry or slip) is significantly more viscous than an unfilled reaction mixture. This typically results in longer build times as the material needs more time to flow into position, requirements of additional mechanical actuation to move the material in place, and difficulty in removing the material from the surface of the part (especially considering a lower green body strength) when shaping of the article is finished.

Reducing the viscosity of the reaction mixture can provide improved performance and efficiency.

Low viscosity sols also allow for simple removal of excess materials from internal channels or deep slots, such as in the case of a narrow wire slot on an orthodontic bracket. Higher viscosity sols combined with a green body of lower mechanical strength make the likelihood of fully realizing the small resolution of channels and dips rather low.

A sol having a viscosity in the ranges described in the present text can be beneficial, e.g. as it can easily flow back over the cured area for producing the next layer.
It can also facilitate better layer adhesion by being more able to intimately wet out the previous cured layer.

The printing sol typically has a viscosity that is sufficiently low so that it can allow for the formation of small, complex features. In many embodiments, the printing sol has a viscosity that is Newtonian or nearly Newtonian like. That is, the viscosity is independent of shear rate or has only a slight dependence on shear rate.

The viscosity can vary depending on the percent solids of the reaction mixture, the size of the zirconia-based particles, the composition of the solvent medium, the presence or absence of optional non-polymerizable surface modification agents, and the composition of the polymerizable material.

The combination of low viscosity and small particle size of the zirconia-based particles advantageously allows the printing sol to be filtered before polymerization. The reaction mixture is often filtered prior to stereolithographic processing. Filtering can be beneficial for removal of debris and impurities that can negatively impact the properties of the gel composition and properties of the sintered article such as optical transmission and strength. Suitable filters often have a pore size of 0.22 µm, 0.45 µm, 1 µm, 2 µm, or 5 µm. Traditional ceramic printing compositions cannot be easily filtered due to particle size and/or viscosity.

In some embodiments, the viscosity of the printing sol is at least 2 mPa*s, at least 5 mPa*s, at least 10 mPa*s, at least 25 mPa*s, at least 50 mPa*s, at least 100 mPa*s, or at least 150 mPa*s. The viscosity can be up to 200 mPa*s, up to 100 mPa*s, up to 50 mPa*s, up to 30 mPa*s, or up to 10 mPa*s. For example, the viscosity can be in a range of 2 to 200 mPa*s, 2 to 100 mPa*s, 2 to 50 mPa*s, 2 to 30 mPa*s, 2 to 20 mPa*s, or 2 to 10 mPa*s.

Processing the printing sol described in the present text in a stereolithography-based process also allows for easy and efficient removal of excess of non-polymerized material from the surface of the printed parts.

The printing sol for use in the additive manufacturing process described in the present text comprises one or more solvents.

The nature and structure of the solvent is not particularly limited unless the desired result cannot be achieved.

In certain embodiments the solvent(s) can be characterized by at least one or more, sometimes all of the following parameters:
Boiling point: above 70 or above 100 or above 120 or above 150° C.;
Molecular weight: from 25 to 300 g/mol or from 30 to 250 g/mol or from 40 to 200 g/mol or from 50 to 175 g/mol;
Viscosity: from 0.1 to 50 or from 0.2 to 10 or from 0.3 to 5 mPa*s (23° C.);
miscible with water;
soluble in supercritical carbon dioxide or liquid carbon dioxide.

Using a solvent with a boiling point above 70 or above 100 or above 150° C. can be beneficial for reducing the risk of evaporation of the solvent during the process.

Using a solvent with a molecular weight and/or viscosity in the above range can be beneficial as it helps adjusting the viscosity of the sol. The molecular weight size can also affect the diffusion constant and how easily the solvent can be removed.

Using a mixture of different solvents can be beneficial as it allows to even further adjust viscosity or post processing properties, e.g. removal of excess sol after printing.

The solvent should be able to dissolve or to disperse the other components being present in the sol.

The solvent should generally also be unreactive towards other components being present in the composition.

The solvent should also be easily removable during the further processing steps needed for the realization of a ceramic article.

Further, the solvent should not interfere with or negatively influence the polymerization of the radiation curable components being present in the sol.

In this respect, using solvents not bearing polymerizable moieties can be beneficial.

To enhance the dissolving capability or property of the solvent, the solvent typically bears one or more polar moieties, including ether, alcohol or carboxy moieties.

According to one embodiment, the solvent is often a glycol or polyglycol, mono-ether glycol or mono-ether polyglycol, di-ether glycol or di-ether polyglycol, ether ester glycol or ether ester polyglycol, carbonate, amide, or sulfoxide (e.g., dimethyl sulfoxide). The organic solvents usually have one or more polar groups. The organic solvent does not have a polymerizable group; that is, the organic solvent is free of a group that can undergo free radical polymerization. Further, no component of the solvent medium has a polymerizable group that can undergo free radical polymerization.

Suitable glycols or polyglycols, mono-ether glycols or mono-ether polyglycols, di-ether glycols or di-ether polyglycols, and ether ester glycols or ether ester polyglycols are often of the following Formula (I).

$$R^1O\text{---}(R^2O)_n\text{---}R^1 \qquad (I)$$

In Formula (I), each $R^1$ independently is hydrogen, alkyl, aryl, or acyl. Suitable alkyl groups often have 1 to 10 carbon atoms, 1 to 6 carbon atoms, or 1 to 4 carbon atoms. Suitable aryl groups often have 6 to 10 carbon atoms and are often phenyl or phenyl substituted with an alkyl group having 1 to 4 carbon atoms. Suitable acyl groups are often of formula —(CO)$R^a$ where $R^a$ is an alkyl having 1 to 10 carbon atoms, 1 to 6 carbon atoms, 1 to 4 carbon atoms, 2 carbon atoms, or 1 carbon atom. The acyl is often an acetyl group (i.e. —C(O)CH$_3$). In Formula (I), each $R^2$ is typically an alkylene group such as ethylene or propylene. The variable n is at least 1 and can be in a range of 1 to 10, 1 to 6, 1 to 4, or 1 to 3.

Glycols or polyglycols of Formula (I) have two $R^1$ groups equal to hydrogen. Examples of glycols include, but are not limited to, ethylene glycol, propylene glycol, diethylene glycol, dipropylene glycol, triethylene glycol, and tripropylene glycol.

Mono-ether glycols or mono-ether polyglycols of Formula (I) have a first $R^1$ group equal to hydrogen and a second $R^1$ group equal to alkyl or aryl. Examples of mono-ether glycols or mono-ether polyglycols include, but are not limited to, ethylene glycol monohexyl ether, ethylene glycol monophenyl ether, propylene glycol monobutyl ether, diethylene glycol monomethyl ether, diethylene glycol monoethyl ether, diethylene glycol monopropyl ether, diethylene glycol monobutyl ether, diethylene glycol monohexyl ether, dipropylene glycol monomethyl ether, dipropylene glycol monoethyl ether, dipropylene glycol monopropyl ether, triethylene glycol monomethyl ether, triethylene glycol monoethyl ether, triethylene glycol monobutyl ether, tripropylene glycol monomethyl ether, and tripropylene glycol monobutyl ether.

Di-ether glycols or di-ether polyglycols of Formula (I) have two R1 group equal to alkyl or aryl. Examples of di-ether glycols or di-ether polyglycols include, but are not limited to, ethylene glycol dipropyl ether, ethylene glycol dibutyl ether, dipropylene glycol dibutyl ether, diethylene glycol dimethyl ether, diethylene glycol diethyl ether, triethylene glycol dimethyl ether, tetraethylene glycol dimethyl ether, and pentaethylene glycol dimethyl ether.

Ether ester glycols or ether ester polyglycols of Formula (I) have a first R1 group equal to an alkyl or aryl and a second R1 group equal to an acyl. Examples of ether ester glycols or ether ester polyglycols include, but are not limited to, ethylene glycol butyl ether acetate, diethylene glycol butyl ether acetate, and diethylene glycol ethyl ether acetate.

Other suitable organic solvents are carbonates of Formula (II).

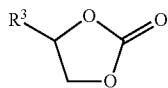

(II)

In Formula (II), $R^3$ is hydrogen or an alkyl such as an alkyl having 1 to 4 carbon atoms, 1 to 3 carbon atoms, or 1 carbon atom. Examples include ethylene carbonate and propylene carbonate.

Yet other suitable organic solvents are amides of Formula (III).

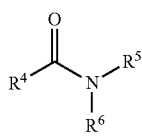

(III)

In Formula (III), group $R^4$ is hydrogen, alkyl, or combines with $R^5$ to form a five-membered ring including the carbonyl attached to $R^4$ and the nitrogen atom attached to $R^5$. Group $R^5$ is hydrogen, alkyl, or combines with $R^4$ to form a five-membered ring including the carbonyl attached to $R^4$ and the nitrogen atom attached to $R^5$. Group $R^6$ is hydrogen or alkyl. Suitable alkyl groups for $R^4$, $R^5$, and $R^6$ have 1 to 6 carbon atoms, 1 to 4 carbon atoms, 1 to 3 carbon atoms, or 1 carbon atom. Examples of amide organic solvents of Formula (III) include, but are not limited to, formamide, N,N-dimethylformamide, N,N-dimethylacetamide, N,N-diethylacetamide, N-methyl-2-pyrrolidone, and N-ethyl-2-pyrrolidone.

Specific examples of solvents which can be used include: mono alcohols (e.g. C2 to C8 alcohols, including primary, secondary and tertiary alcohols), poly alcohols (e.g. ethylene glycol, propylene glycol, glycerine, diethylene glycol ethyl ether (Carbitol™), 1-methoxy-2-propanol, N-methyl pyrrolidone acetonitrile, chlorobenzene, 1,4-dioxane, ethyl acetate, methyl ethyl ketone, tetrahydrofuran, toluene, xylene and mixtures thereof.

The following solvents are sometimes preferred: ethanol, 1-methoxy-2-propanol, N-methyl pyrrolidone, diethylene glycol ethyl ether, and mixtures thereof. In some situations, suitable solvents may also include low boiling alcohols (below 100° C.; like methanol, ethanol, propanol) and mixtures thereof or preferably the same solvent(s) described above.

The solvent(s) is typically present in the following amounts:
Lower amount: at least 25 or at least 30 or at least 35 wt.-%;
Upper amount: at most 70 or at most 65 or at most 60 wt.-%;
Range: from 25 to 70 or from 30 to 65 or from 35 to 60 or from 35 to 55 or from 35 to 50 wt.-%;
wt.-% with respect to the weight of the printing sol.

In one embodiment, the printing sol for use in the additive manufacturing process described in the present text comprises nano-sized zirconia particles.

The nature and structure of the nano-sized zirconia particles is not particularly limited unless the desired result cannot be achieved.

The printing sol preferably comprises zirconia crystallites having a certain tetragonal phase content and a sol comprising zirconia crystallites having a certain cubic phase content.

In certain embodiments the nano-sized zirconia particles(s) can be characterized by at least one or more, sometimes all of the following parameters or features:
Primary particle size XRD (diameter): from 2 to 50 or from 2 to 20 nm or from 2 to 15 or from 4 to 15 nm;
being essentially spherical, cuboid or a mixture of spherical and cuboid;
being non-associated;
being crystalline;
not being coated with an inorganic coloring agent.
"Essentially spherical" means that the shape of the particles is close to a sphere. It does not contain sharp edges, which may result from a milling process.

The nano-sized zirconia particles contained in the sol can be characterized by at least one or more or all of the following features:
$ZrO_2$ content: from 70 to 100 mol-% or from 80 to 97 mol-%;
$HfO_2$ content: from 0 to 4.5 mol-% or from 0 to 3 mol-% or from 0.1 to 2.8 mol-%;
Stabilizer selected from $Y_2O_3$, $CeO_2$, MgO, CaO, $La_2O_3$ or a combination thereof in an amount from 0 to 30 mol-% or from 1.5 to 16 mol-% or from 2 to 10 mol-% or 2 to 5 mol-%;
$Al_2O_3$ content: from 0 to 1 mol-% or from 0.005 to 0.5 mol-% or from 0.01 to 0.2 mol-%.

According to one embodiment, the nano-sized zirconia particles are characterized as follows: $ZrO_2$ content: from 70 to 98.4 mol-%; $HfO_2$ content: from 0.1 to 2.8 mol-%; $Y_2O_3$ content: from 1.5 to 20 mol-%.

The nano-sized zirconia particles can be obtained or are obtainable by a process comprising the steps of hydrothermal treatment of an aqueous metal salt solution or suspension (e.g. zirconium salt, yttrium salt). Such a process is described in WO 2013/055432 (3M), the content of which is herewith incorporated by reference.

With respect to wt.-%, the printing sol used to form the gel composition typically contains 20 to 70 wt.-% zirconia-based particles based on a total weight of the printing sol. The amount of zirconia-based particles can be at least 25 wt.-%, at least 30 wt.-%, at least 35 wt.-%, or at least 40 wt.-% and can be up to 55 wt.-%, up to 50 wt.-%, or up to 45 wt.-%. In some embodiments, the amount of the zirconia-based particles are in a range of 25 to 55 wt.-%, 30 to 50 wt.-%, 30 to 45 wt.-%, 35 to 50 wt.-%, 40 to 50 wt.-%, or 35 to 45 wt.-% based on the total weight of the printing sol. If expressed in vol.-%, the amount of the zirconia-based particles is as follows:

Lower amount: at least 2 or at least 4 or at least 5 vol.-%;
Upper amount: at most 25 or at most 18 at most 16 vol.-%;
Range: from 2 to 25 or from 4 to 18 vol.-% or from 5 to 16 vol.-%;
vol.-% with respect to the volume of the printing sol.

Compared to zirconia containing slurries or slips described in the prior art (e.g. U.S. Pat. No. 7,927,538 B2), the printing sol described in the present text contains the zirconia particles in only a comparably low volume content. This facilitates adjusting the sol to a desired low viscosity, which may contribute to an easier processing. It may also allow the manufacturing of 3-dim articles in an enlarged state, which can be sintered to the desired dimension later, as described later in the text.

The printing sol described in the present text comprises one or more radiation curable monomers being part of or forming an organic matrix.

The radiation curable monomers being present in the printing sol can be described as first, second, third, etc. monomer.

The nature and structure of the radiation curable monomer(s) is not particularly limited unless the desired result cannot be achieved.

Upon polymerization, the radiation curable monomers form a network with the homogeneously dispersed nano-sized zirconia particles.

According to one embodiment the printing sol described in the present text contains as a first monomer a polymerizable surface modification agent.

A surface modification agent may help to improve compatibility of the zirconia particles contained in the sol with an organic matrix material being present in the sol as well.

Surface modification agents may be represented by the formula A-B, where the A group is capable of attaching to the surface of a zirconia-based particle and the B group is radiation curable.

Group A can be attached to the surface of the zirconia-based particle by adsorption, formation of an ionic bond, formation of a covalent bond, or a combination thereof.

Examples for Group A include acidic moieties (like carboxylic acid groups, phosphoric acid groups, sulfonic acid groups and anions thereof) and silanes.

Group B comprises a radiation curable moiety.

Examples for Group B include vinyl, in particular acryl or methacryl moieties.

Suitable surface modifying agents comprise polymerizable carboxylic acids and/or anions thereof, polymerizable sulfonic acids and/or anions thereof, polymerizable phosphoric acids and/or anions thereof, and polymerizable silanes. Suitable surface modification agents are further described, for example, in WO 2009/085926 (Kolb et al.), the disclosure of which is incorporated herein by reference.

An example of a radically polymerizable surface modifier is a polymerizable surface modification agent comprising an acidic moiety or anion thereof, e.g. a carboxylic acid group.

Exemplary acidic radically polymerizable surface modifiers include acrylic acid, methacrylic acid, beta-carboxyethyl acrylate, and mono-2-(methacryloxyethyl)succinate.

Exemplary radically polymerizable surface modifiers can be reaction products of hydroxyl-containing polymerizable monomers with cyclic anhydrides such as succinic anhydride, maleic anhydride and phthalic anhydride. Exemplary polymerization hydroxyl-containing monomers include hydroxyethyl acrylate, hydroxyethyl methacrylate, hydroxypropyl acrylate, hydroxypropyl methacrylate, hydroxyl butyl acrylate, and hydroxybutyl methacrylate. Acryloxy and methacryloxy functional polyethylene oxide, and polypropylene oxide may also be used as the polymerizable hydroxyl-containing monomers.

An exemplary radically polymerizable surface modifier for imparting both polar character and reactivity to the zirconia-containing nanoparticles is mono(methacryloxy-polyethyleneglycol) succinate.

Another example of a radically polymerizable surface modifier is a polymerizable silane.

Exemplary polymerizable silanes include methacryloxy-alkyltrialkoxysilanes, or acryloxyalkyltrialkoxysilanes (e.g., 3-methacryloxypropyltrimethoxysilane, 3-acryloxypropyltrimethoxysilane, and 3-(methacryloxy)propyltriethoxysilane; as 3-(methacryloxy)propylmethyldimethoxysilane, and 3-(acryloxypropyl)methyldimethoxysilane); methacryloxyalkyldialkylalkoxysilanes or acyrloxyalkyldialkylalkoxysilanes (e.g., 3-(methacryloxy)propyldimethylethoxysilane); mercaptoalkyltrialkoxylsilanes (e.g., 3-mercaptopropyltrimethoxysilane); aryltrialkoxysilanes (e.g., styrylethyltrimethoxysilane); vinylsilanes (e.g., vinylmethyldiacetoxysilane, vinyldimethylethoxysilane, vinylmethyldiethoxysilane, vinyltrimethoxysilane, vinyltriethoxysilane, vinyltriacetoxysilane, vinyltriisopropoxysilane, vinyltrimethoxysilane, and vinyltris(2-methoxyethoxy)silane).

A surface modification agent can be added to the zirconia-based particles using conventional techniques. The surface modification agent can be added before or after any removal of at least a portion of the carboxylic acids and/or anions thereof from the zirconia-based sol. The surface modification agent can be added before or after removal of the water from the zirconia-based sol. The organic matrix can be added before or after surface modification or simultaneously with surface modification. Various methods of adding the surface modification agent are further described, for example, in WO 2009/085926 (Kolb et al.), the disclosure of which is incorporated herein by reference.

The surface modification reactions can occur at room temperature (e.g., 20° C. to 25° C.) or at an elevated temperature (e.g., up to 95° C.). When the surface modification agents are acids such as carboxylic acids, the zirconia-based particles typically can be surface-modified at room temperature. When the surface modification agents are silanes, the zirconia-based particles are typically surface modified at elevated temperatures.

The first monomer can function as a polymerizable surface modification agent. Multiple first monomers can be used. The first monomer can be the only kind of surface modification agent or can be combined with one or more other non-polymerizable surface modification agents. In some embodiments, the amount of the first monomer is at least 20 wt.-% based on a total weight of polymerizable material. For example, the amount of the first monomer is often at least 25 wt.-%, at least 30 wt.-%, at least 35 wt.-%, or at least 40 wt.-%. The amount of the first monomer can be up to 100 wt.-%, up to 90 wt.-%, up to 80 wt.-%, up to 70 wt.-%, up to 60 wt.-%, or up to 50 wt.-%. Some printing sols contain 20 to 100 wt.-%, 20 to 80 wt.-%, 20 to 60 wt.-%, 20 to 50 wt.-%, or 30 to 50 wt.-% of the first monomer based on a total weight of polymerizable material.

The first monomer (i.e. the polymerizable surface modification agent) can be the only monomer in the polymerizable material or it can be combined with one or more second monomers that are soluble in the solvent medium.

According to one embodiment, the printing sol described in the present text comprises one or more second monomers comprising at least one or two radiation curable moieties. In particular the second monomers comprising at least two radiation curable moieties may act as crosslinker(s) during the gel-forming step.

Any suitable second monomer that does not have a surface modification group can be used. The second monomer does not have a group being capable of attaching to the surface of a zirconia-based particle.

A successful build typically requires a certain level of green body gel strength as well as shape resolution. A crosslinked approach often allows for greater green body gel strength to be realized at a lower energy dose since the polymerization creates a stronger network. In some examples, higher energy doses have been applied to increase layer adhesion of non crosslinked systems. While an article is successfully built, the higher energy often impacts the resolution of the final article, causing overbuild to potentially occur, especially in the case of highly translucent materials where the light and with it the cure depth can penetrate further into the material.

The presence of the monomer having a plurality of polymerizable groups tends to enhance the strength of the gel composition formed when the printing sol is polymerized. Such gel compositions can be easier to process without cracking. The amount of the monomer with a plurality of polymerizable groups can be used to adjust the flexibility and the strength of the green body gel, and indirectly optimize the green body gel resolution and final article resolution.

In the case where the light source is applied from below, it was found that applying e.g. crosslink chemistry may help to increase the strength of the adhesion between layers so that when the build platform is raised after the cure step, the newly cured layer moves with the building shape, rather than being separated from the rest of the build and left behind on the transparent film, which would be considered a failed build.

A successful build could be defined as the scenario when the material adheres better to the previously cured layers than the build tray film to allow for a three-dimensional structure to be grown one layer at a time.

This performance could in theory be achieved by applying an increased energy dose (higher power, or longer light exposure) to provide a stronger adhesion up to a certain point characteristic of the bulk material. However, in a fairly transparent system where light absorbing additives are not present a higher energy exposure will eventually provide a depth of cure significantly greater than the 'slice thickness' creating an over-cured situation where the resolution of the part is significantly beyond that of the 'slice thickness'.

Adding a radiation curable component comprising at least two radiation curable moieties to the printing sol described in the present text may facilitate the optimization of resolution as well as green body strength.

In the case of transforming the green body into a fully dense ceramic, increased green body gel strength aids in the robustness of the post-building procedures.

That is, the optional second monomer does not have a carboxylic acid group or a silyl group. The second monomers are often polar monomers (e.g., non-acidic polar monomers), monomers having a plurality of polymerizable groups, alkyl (meth)acrylates and mixtures thereof.

The overall composition of the polymerizable material is often selected so that the polymerized material is soluble in the solvent medium. Homogeneity of the organic phase is often preferable to avoid phase separation of the organic component in the gel composition. This tends to result in the formation of smaller and more homogeneous pores (pores with a narrower size distribution) in the subsequently formed aerogel. Further, the overall composition of the polymerizable material can be selected to adjust compatibility with the solvent medium and to adjust the strength, flexibility, and uniformity of the gel composition. Still further, the overall composition of the polymerizable material can be selected to adjust the burnout characteristics of the organic material prior to sintering.

In many embodiments, the second monomer includes a monomer having a plurality of polymerizable groups. The number of polymerizable groups can be in a range of 2 to 6 or even higher. In many embodiments, the number of polymerizable groups is in a range of 2 to 5 or 2 to 4. The polymerizable groups are typically (meth)acryloyl groups.

Exemplary monomers with two (meth)acryloyl groups include 1,2-ethanediol diacrylate, 1,3-propanediol diacrylate, 1,9-nonanediol diacrylate, 1,12-dodecanediol diacrylate, 1,4-butanediol diacrylate, 1,6-hexanediol diacrylate, butylene glycol diacrylate, bisphenol A diacrylate, diethylene glycol diacrylate, triethylene glycol diacrylate, tetraethylene glycol diacrylate, tripropylene glycol diacrylate, polyethylene glycol diacrylate, polypropylene glycol diacrylate, polyethylene/polypropylene copolymer diacrylate, polybutadiene di(meth)acrylate, propoxylated glycerin tri(meth) acrylate, and neopentylglycol hydroxypivalate diacrylate modified caprolactone.

Exemplary monomers with three or four (meth)acryloyl groups include, but are not limited to, trimethylolpropane triacrylate (e.g., commercially available under the trade designation TMPTA-N from Cytec Industries, Inc. (Smyrna, Ga., USA) and under the trade designation SR-351 from Sartomer (Exton, Pa., USA)), pentaerythritol triacrylate (e.g., commercially available under the trade designation SR-444 from Sartomer), ethoxylated (3) trimethylolpropane triacrylate (e.g., commercially available under the trade designation SR-454 from Sartomer), ethoxylated (4) pentaerythritol tetraacrylate (e.g., commercially available under the trade designation SR-494 from Sartomer), tris(2-hydroxyethylisocyanurate) triacrylate (e.g., commercially available under the trade designation SR-368 from Sartomer), a mixture of pentaerythritol triacrylate and pentaerythritol tetraacrylate (e.g., commercially available from Cytec Industries, Inc., under the trade designation PETIA with an approximately 1:1 ratio of tetraacrylate to triacrylate and under the trade designation PETA-K with an approximately 3:1 ratio of tetraacrylate to triacrylate), pentaerythritol tetraacrylate (e.g., commercially available under the trade designation SR-295 from Sartomer), and di-trimethylolpropane tetraacrylate (e.g., commercially available under the trade designation SR-355 from Sartomer).

Exemplary monomers with five or six (meth)acryloyl groups include, but are not limited to, dipentaerythritol pentaacrylate (e.g., commercially available under the trade designation SR-399 from Sartomer) and a hexa-functional urethane acrylate (e.g., commercially available under the trade designation CN975 from Sartomer).

Some printing sol compositions contain 0 to 80 wt.-% of a second monomer having a plurality of polymerizable groups based on a total weight of the polymerizable material. For example, the amount can be in a range of 10 to 80 wt.-%, 20 to 80 wt.-%, 30 to 80 wt.-%, 40 to 80 wt.-%, 10 to 70 wt.-%, 10 to 50 wt.-%, 10 to 40 wt.-%, or 10 to 30 wt.-%.

In some embodiments, the optional second monomer is a polar monomer. As used herein, the term "polar monomer" refers to a monomer having a free radical polymerizable group and a polar group. The polar group is typically non-acidic and often contains a hydroxyl group, a primary amido group, a secondary amido group, a tertiary amido group, an amino group, or an ether group (i.e., a group containing at least one alkylene-oxy-alkylene group of formula —R—O—R— where each R is an alkylene having 1 to 4 carbon atoms).

Suitable optional polar monomers having a hydroxyl group include, but are not limited to, hydroxyalkyl (meth)acrylates (e.g., 2-hydroxyethyl (meth)acrylate, 2-hydroxypropyl (meth)acrylate, 3-hydroxypropyl (meth)acrylate, and 4-hydroxybutyl (meth)acrylate), and hydroxyalkyl (meth)acrylamides (e.g., 2-hydroxyethyl (meth)acrylamide or 3-hydroxypropyl (meth)acrylamide), ethoxylated hydroxyethyl (meth)acrylate (e.g., monomers commercially available from Sartomer (Exton, Pa., USA) under the trade designation CD570, CD571, and CD572), and aryloxy substituted hydroxyalkyl (meth)acrylates (e.g., 2-hydroxy-2-phenoxypropyl (meth)acrylate).

Exemplary polar monomers with a primary amido group include (meth)acrylamide. Exemplary polar monomers with secondary amido groups include, but are not limited to, N-alkyl (meth)acrylamides such as N-methyl(meth)acrylamide, N-ethyl (meth)acrylamide, N-isopropyl (meth)acrylamide, N-tert-octyl (meth)acrylamide, and N-octyl (meth)acrylamide. Exemplary polar monomers with a tertiary amido group include, but are not limited to, N-vinyl caprolactam, N-vinyl-2-pyrrolidone, (meth)acryloyl morpholine, and N,N-dialkyl (meth)acrylamides such as N,N-dimethyl (meth)acrylamide, N,N-diethyl(meth)acrylamide, N,N-dipropyl(meth)acrylamide, and N,N-dibutyl(meth)acrylamide.

Polar monomers with an amino group include various N,N-dialkylaminoalkyl (meth)acrylates and N,N-dialkylaminoalkyl (meth)acrylamides. Examples include, but are not limited to, N,N-dimethyl aminoethyl (meth)acrylate, N,N-dimethylaminoethyl (meth)acrylamide, N,N-dimethylaminopropyl(meth)acrylate, N,N-dimethylaminopropyl (meth)acrylamide, N,N-diethylaminoethyl(meth)acrylate, N,N-diethylaminoethyl (meth)acrylamide, N,N-diethylaminopropyl(meth)acrylate, and N,N-diethylaminopropyl (meth)acrylamide.

Exemplary polar monomers with an ether group include, but are not limited to, alkoxylated alkyl (meth)acrylates such as ethoxyethoxyethyl (meth)acrylate, 2-methoxyethyl (meth)acrylate, and 2-ethoxyethyl (meth)acrylate; and poly (alkylene oxide) (meth)acrylates such as poly(ethylene oxide) (meth)acrylates, and poly(propylene oxide) (meth)acrylates. The poly(alkylene oxide) acrylates are often referred to as poly(alkylene glycol) (meth)acrylates. These monomers can have any suitable end group such as a hydroxyl group or an alkoxy group. For example, when the end group is a methoxy group, the monomer can be referred to as methoxy poly(ethylene glycol) (meth)acrylate.

Suitable alkyl (meth)acrylates that can be used as a second monomer can have an alkyl group with a linear, branched, or cyclic structure. Examples of suitable alkyl (meth)acrylates include, but are not limited to, methyl(meth)acrylate, ethyl (meth)acrylate, n-propyl (meth)acrylate, isopropyl (meth)acrylate, n-butyl (meth)acrylate, isobutyl (meth)acrylate, n-pentyl (meth)acrylate, 2-methylbutyl (meth)acrylate, n-hexyl (meth)acrylate, cyclohexyl (meth)acrylate, 4-methyl-2-pentyl (meth)acrylate, 2-ethylhexyl (meth)acrylate, 2-methylhexyl (meth)acrylate, n-octyl (meth)acrylate, isooctyl (meth)acrylate, 2-octyl (meth)acrylate, isononyl (meth)acrylate, isoamyl (meth)acrylate, 3,3,5-trimethylcyclohexyl (meth)acrylate, n-decyl (meth)acrylate, isodecyl (meth)acrylate, isobornyl (meth)acrylate, 2-propylheptyl (meth)acrylate, isotridecyl (meth)acrylate, isostearyl (meth)acrylate, octadecyl (meth)acrylate, 2-octyldecyl (meth)acrylate, dodecyl (meth)acrylate, lauryl (meth) acrylate, and heptadecanyl (meth)acrylate.

The amount of a second monomer that is a polar monomer and/or an alkyl (meth)acrylate monomer is often in a range of 0 to 40 wt.-%, 0 to 35 wt.-%, 0 to 30 wt.-%, 5 to 40 wt.-%, or 10 to 40 wt.-% based on a total weight of the polymerizable material.

The total amount of polymerizable material is often at least 2 wt.-%, at least 3 wt.-%, at least 5 wt.-%, or at least 10 wt.-% based on the total weight of the printing sol. The amount of polymerizable material can be up to 30 wt.-%, up to 25 wt.-%, up to 20 wt.-%, or up to 15 wt.-% based on the total weight of the printing sol. For example, the amount of polymerizable material can be in a range of 2-30 wt.-%, 3-20 wt.-%, or 5-15 wt.-% based on the total weight of the printing sol.

Overall, the polymerizable material typically contains 20 to 100 wt.-% first monomer and 0 to 80 wt.-% second monomer based on a total weight of polymerizable material. For example, polymerizable material includes 30 to 100 wt.-% first monomer and 0 to 70 wt.-% second monomer, 30 to 90 wt.-% first monomer and 10 to 70 wt.-% second monomer, 30 to 80 wt.-% first monomer and 20 to 70 wt.-% second monomer, 30 to 70 wt.-% first monomer and 30 to 70 wt.-% second monomer, 40 to 90 wt.-% first monomer and 10 to 60 wt.-% second monomer, 40 to 80 wt.-% first monomer and 20 to 60 wt.-% second monomer, 50 to 90 wt.-% first monomer and 10 to 50 wt.-% second monomer, or 60 to 90 wt.-% first monomer and 10 to 40 wt.-% second monomer.

In some applications, it can be advantageous to minimize the weight ratio of polymerizable material to zirconia-based particles in the reaction mixture. This tends to reduce the amount of decomposition products of organic material that needs to be burned out prior to formation of the sintered article. The weight ratio of polymerizable material to zirconia-based particles is often at least 0.05, at least 0.08, at least 0.09, at least 0.1, at least 0.11, or at least 0.12. The weight ratio of polymerizable material to zirconia-based particles can be up to 0.8, up to 0.6, up to 0.4, up to 0.3, up to 0.2, or up to 0.1. For example, the ratio can be in a range of 0.05 to 0.8, 0.05 to 0.6, 0.05 to 0.4, 0.05 to 0.2, 0.05 to 0.1, 0.1 to 0.8, 0.1 to 0.4, or 0.1 to 0.3.

In certain embodiments the second monomer(s) can be characterized by at least one or more, sometimes all of the following parameters:
- soluble in the solvent contained in the sol;
- bearing at least one or two or three radiation curable moieties;
- bearing radiation curable moieties selected from vinyl, acryl or methacryl moieties;
- molecular weight from 70 to 5,000 or from 70 to 1,000 g/mol or from 100 to 500 g/mol.

Using radiation curable component(s) as described above having a molecular weight in the above range facilitates the provision of a sol having the desired viscosity. Lower molecular weight components are typically also better soluble than high molecular weight components.

If present, the second monomer is typically present in the following amounts:
Lower amount: at least 0.5 or at least 1 or at least 3 wt.-%;
Upper amount: at most 5 or at most 10 or at most 24 wt.-%;
Range: from 0.5 to 24 or from 3 to 10 wt.-%;
wt.-% with respect to the weight of the printing sol.

Methods for adding a radiation curable monomer(s) to the nanoparticles are known in the art. The radiation curable monomer(s) can be added, for example, before or after any removal of at least a portion of the carboxylic acids and/or anions thereof from the zirconia-containing sol. The radiation curable component can be added, for example, before or after removal of the water from the zirconia-containing sol.

The radiation curable components can be added directly to the nanoparticles containing sol. The radiation curable monomer(s) that are added are subsequently polymerized and/or crosslinked to form a gel.

The printing sol described in the present text comprises one or more photoinitiator(s).

The nature and structure of the photoinitiator is not particularly limited, either, unless the desired result cannot be achieved.

In certain embodiments the photoinitiator(s) can be characterized by at least one or more, sometimes all of the following parameters:
- Soluble in the solvent contained in the sol;
- Radiation absorption: within a range from 200 to 500 or from 300 to 450 nm.

The photoinitiator should be able to start or initiate the curing or hardening reaction of the radiation curable component(s) being present in the printing sol.

The following classes of photoinitiator(s) can be used: a) two-component system where a radical is generated through abstraction of a hydrogen atom from a donor compound; b) one component system where two radicals are generated by cleavage.

Examples of photoiniators according to type (a) typically contain a moiety selected from benzophenone, xanthone or quinone in combination with an aliphatic amine.

Examples of photoinitiators according to type (b) typically contain a moiety selected form benzoin ether, acetophenon, benzoyl oxime or acyl phosphine.

Exemplary UV initiators include 1-hydroxycyclohexyl benzophenone (available, for example, under the trade designation "IRGACURE 184" from Ciba Specialty Chemicals Corp., Tarrytown, N.Y.), 4-(2-hydroxyethoxy)phenyl-(2-hydroxy-2-propyl) ketone (available, for example, under the trade designation "IRGACURE 2529" from Ciba Specialty Chemicals Corp.), 2-hydroxy-2-methylpropiophenone (available, for example, under the trade designation "DAROCURE D111" from Ciba Specialty Chemicals Corp. and bis(2,4,6-trimethylbenzoyl)-phenylposphineoxide (available, for example, under the trade designation "IRGACURE 819" from Ciba Specialty Chemicals Corp.).

The photoinitiator(s) is typically present in the following amounts:
Lower amount: at least 0.01 or at least 0.05 or at least 0.1 wt.-%;
Upper amount: at most 0.5 or at most 1 or at most 3 wt.-%;
Range: from 0.01 to 3 or from 0.01 to 1 wt.-% or 0.01 to 0.5 wt.-%;
wt.-% with respect to the weight of the printing sol.

The printing sol described in the present text may also comprise one or more organic dye(s).

The nature and structure of the organic dye(s) is not particularly limited unless the desired result cannot be achieved.

It was found that by adding an organic dye, the ability of the translucent sol described in the present text to absorb radiation can be enhanced.

In addition, it was found that adding an organic dye contributes to suppress or to lower the transmission of scattered light in the sol. This often helps to improve the accuracy or detail resolution of the surface of the ceramic article obtained from the additive manufacturing process.

In certain embodiments the organic dye(s) can be characterized by at least one, more, of all of the following parameters:
- soluble in the solvent contained in the sol;
- radiation absorption: within a range from 200 to 500 or from 300 to 450 nm;
- combustible without residues at temperature below 800° C.;
- having a molecular weight in the range of 50 to 1,000 g/mol.

The organic dye does typically not contain elements or ions other than alkaline metal ions (e.g. Li, Na, K), earth alkaline metal ions (e.g. Mg, Ca), C, N, O, H, S, P, halogen (F, Cl, Br). That is, the organic dye molecule does typically not contain any heavy metal ions (e.g. metal ions having an atomic mass above 40 or above 45.

Dyes which can be used include those containing a moiety selected form azo groups and/or aromatic (hetero) cycles or other systems with delocalized pi-electrons. In particular dyes useful for colouring food were found to be useful.

Specific examples of dye(s) which can be used include riboflavin (E101), tartrazine (E102), isatin, azorubin (E122) and combinations thereof.

If present, the organic dye(s) is present in the following amounts:
Lower amount: at least 0.001 or at least 0.002 or at least 0.005 wt.-%;
Upper amount: at most 0.5 or at most 0.2 or at most 0.1 wt.-%;
Range: from 0.001 to 0.5 or from 0.002 to 0.2 or 0.005 to 0.1 wt.-%;
wt.-% with respect to the weight of the printing sol.

According to a further embodiment, the printing sol described in the present text comprises one or more inhibitor(s).

The nature and structure of the inhibitor(s) is not particularly limited, either, unless the desired result cannot be achieved.

An inhibitor may extend the shelf life of the printing sol, help prevent undesired side reactions, and adjust the polymerization process of the radiation curable component(s) present in the sol.

Adding one or more inhibitor(s) to the printing sol may further help to improving the accuracy or detail resolution of the surface of the ceramic article.

In particular it was found that adding inhibitor(s) to the printing sol described in the present text may help to enhance the resolution and accuracy of the SLA process by attenuating or avoiding unwanted scattering effects, as well as increase the shelf life of the printing sol.

The inhibitor(s) should be soluble in the solvent contained in the sol. Inhibitors which can be used often comprise a phenol moiety.

Specific examples of inhibitor(s) which can be used include: p-methoxyphenol (MOP), hydroquinone monomethylether (MEHQ), 2,6-di-tert-butyl-4-methyl-phenol (BHT; Ionol), phenothiazine, 2,2,6,6-tetramethyl-piperidine-1-oxyl radical (TEMPO) and mixtures thereof.

If present, the inhibitor(s) is present in the following amounts:

Lower amount: at least 0.001 or at least 0.005 or at least 0.01 wt.-%;

Upper amount: at most 0.02 or at most 0.05 or at most 0.5 at most 1 wt.-%;

Range: from 0.001 to 1 or from 0.005 to 0.05 wt.-%;

wt.-% with respect to the weight of the printing sol.

According to one embodiment, the printing sol described in the present text used as construction material in the additive manufacturing process is characterized as follows:
  Solvent content: from 25 to 70 or from 40 to 65 wt.-%; the sol having preferably a boiling point above 70° C. and being selected from alcohols and glycol ethers;
  Polymerizable material content: from 2 to 30 wt.-%, or from 3 to 20 wt.-% or from 5 to 15 wt.-%, the polymerizable material comprising a first monomer having at least one radiation curable moiety and an acidic or silyl moiety;
  Photoinitiator content: from 0.01 to 3 or from 0.5 to 1.5 wt.-%;
  Nano-sized crystalline zirconia particles content: from 20 to 70, or from 30 to 50 wt.-%;
  Inhibitor content: from 0 to 0.25 or from 0.001 to 0.15 wt.-%;
  Organic dye content: from 0 to 0.2 or from 0.01 to 0.1 wt.-%;
  wt.-% with respect to the weight of the printing sol.

The sol described in the present text does typically not comprise one or more or all of the following components:
  wax(es) in an amount of more than 0.1 wt.-% or more than 0.01 wt.-%;
  insoluble pigment(s) in an amount of more than 0.5 wt.-% or 0.1 or 0.01 wt.-%;
  stabilizers comprising an N,N-dialkylamine group in an amount of more than 0.5 wt.-% or 0.1 or 0.01 wt.-%;
  wt.-% with respect to the weight of the printing sol.

Adding those components to the sol described in the present text may result in a composition, the processing of which may cause problems in additive manufacturing processes.

In particular components being insoluble in the solvent like pigment(s) can sometimes cause problems, e.g. due to light scattering.

The sol described in the present text can be obtained as follows:

A starting sol containing nano-sized particles as described in the present text is provided.

To this starting sol the other components are added: the radiation curable component(s), the photoinitiator(s), and optionally organic dye(s), optionally inhibitor(s) and optionally inorganic colouring agent(s), if desired.

The preparation of the sol is typically conducted under save light conditions to avoid an undesired early polymerization.

The sol is typically stored in a suitable device like a vessel, a bottle, cartridge or container before use.

Sols which were found to be suitable as well are described e.g. in WO 2013/055432 (3M) relating to aerogels, calcined articles and crystalline articles comprising zirconia and a methods of making the same. U.S. Pat. No. 7,429,422 (Davidson et al.) also describes methods of making zirconia-based sols, which can be used. Further sols which can be used are described in U.S. application No. 62/127,569 (3M) filed Mar. 3, 2015. The above references are herewith incorporated by reference.

The invention is also directed to a ceramic article obtained or obtainable by a process as described in the present text. According to one embodiment, the ceramic article is a dental or orthodontic ceramic article.

In certain embodiments the ceramic article can be characterized by at least one or more, sometimes all of the following parameters:
  density: at least about 98.5 (in some embodiments, 99, 99.5, 99.9, or even at least 99.99) percent of theoretical density;
  Vickers hardness: from 450 MPa to 2,200 MPa, or from 500 MPa to 1,800 MPa·HV(2);
  phase content: tetragonal phase: from 0 to 100 wt.-% or from 10 to 100 wt.-%; cubic phase: from 0 to 100 wt.-% or from 50 to 90 wt.-%;
  flexural strength: from 450 MPa to 2,200 MPa, or from 500 MPa to 2,000 MPa; according to ISO 6872;
  translucency: more than 30% determined on a polished sample having a thickness of 1 mm;
  at least one of the x, y, z dimensions being at least 0.25 or at least 1 mm.

The average grain size is often in a range of 75 nm to 400 nm or in a range of 100 nm to 400 nm. The grain size is typically no greater than 400 nm, no greater than 350 nm, no greater than 300 nm, no greater than 250 nm, no greater than 200 nm, or no greater than 150 nm. It is assumed that this grain size contributes to the high strength of the sintered articles.

The ceramic article obtainable or obtained according to the process described in the present text often shows a laminated structure, if cut in longitudinal direction. Longitudinal direction means the direction according to which the additive manufacturing process took place.

In certain embodiments the ceramic article can be characterized by at least one or more, sometimes all of the following features:
  $ZrO_2$ content: from 70 to 100 mol-% or from 80 to 97 mol-%;
  $HfO_2$ content: from 0 to 4.5 mol-% or from 0 to 3 mol-% or from 0.1 to 2.8 mol-%;
  Stabilizer selected from $Y_2O_3$, $CeO_2$, MgO, CaO, $La_2O_3$ or a combination thereof in an amount from 0 to 30 mol-% or from 1.5 to 20 mol-% or from 2 to 10 mol-% or 2 to 5 mol-%;
  $Al_2O_3$ content: from 0 to 1 mol-% or from 0.005 to 0.5 mol-% or from 0.01 to 0.2 mol-%;
  optionally comprising oxides of elements selected from Er, Tb, Mn, Bi, Nd, Fe, Pr, Co, Cr, V, Cu, Eu, Sm, Dy, Tb, preferably Fe, Mn, Er, Pr, Tb and combinations thereof.

The ceramic article may have different shapes.

According to one embodiment, the ceramic article has the shape of a dental ceramic article, in particular the shape of a dental restoration (including the shape of a dental crown, bridge, inlay, onlay, veneer, implant as described above) or orthodontic bracket.

All components used in the dental composition of the invention should be sufficiently biocompatible, that is, the composition should not produce a toxic, injurious, or immunological response in living tissue.

The production of the ceramic article does typically not require the application of a hot isostatic pressing step (HIP).

According to one embodiment, the process for producing a ceramic article as described in the present text does not comprise either or all of the following steps.

heating the construction material during the processing step to a temperature above 70° C.;
applying pressure during the sintering process.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention. Unless otherwise indicated, all parts and percentages are by weight.

The invention described in the present text is also directed to the following embodiments:

Embodiment OD1

A process for producing a ceramic article, the process comprising the steps of:
providing a printing sol, the printing sol comprising nano-sized zirconia particles, radiation curable components and a photo initiator system,
processing the printing sol as construction material in an additive manufacturing process to obtain a 3-dim article being in a gel state, the 3-dim article having a Volume A,
applying a supercritical drying step to the 3-dim article being in a gel state,
applying a heat treatment step to obtain a sintered 3-dim ceramic article having the Volume F.

Embodiment OD2

The process according to preceding embodiment, Volume A of the 3-dim article in a gel state being more than 200% of the Volume F of the 3-dim article in its sintered state.

The printing sol described in the Embodiments OD1 to OD8 can be produced and processed in the same manner as described for the other printing sols of the present text.

The invention also relates to a process of producing a 3-dim article, the process comprising the step of processing a printing sol as described in the present text by using or applying an additive manufacturing technique as described in the present text.

The invention is also directed to a zirconia gel body obtainable or obtained according to the process described in the present text, the zirconia gel body being preferably a zirconia aerogel body or zirconia xerogel body.

Examples

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

The following examples are given to illustrate, but not limit, the scope of this invention.

Materials

| Material or abbreviation | Description |
| --- | --- |
| MEEAA | 2-(2-(2-Methoxyethoxy) Ethoxy) Acetic Acid |
| Zirconium acetate | An aqueous solution of zirconium acetate containing nominally 16.3 weight percent zirconium obtained from Magnesium Elektron, Inc., Flemington, NJ, USA. The aqueous solution was exposed to an ion exchange resin (obtained under the trade designation "AMBERLYTE IR 120" from Rohm and Haas Company, Philadelphia, PA, USA) before use (oxide content 21.85 wt. %). |
| Lanthanum Oxide | Lanthanum (III) oxide (99% rare earth oxides) |
| Yttrium acetate | Yttrium (III) acetate tetrahydrate (oxide content 33.4 wt. %). |
| Lanthanum Acetate | Lathanum (III) acetate hydrate (oxide content 45.5 wt. %) |
| DI water | De-ionized water. |
| HEMA | 2-Hydroxyethyl methacrylate |
| Irgacure ™ 819 | UV/Visible photoinitiator from BASF |
| HEAA | N-(2-Hydroxyethyl) acrylamide |
| MOP | Methoxyphenol |

Methods

Method for Determining Total Pore Volume, Average Connected Pore Diameter and BET Surface Area Total pore volume and average pore diameter were analyzed with the use of $N_2$ sorption Isotherms and BET surface area analysis. Samples of around 0.3-0.5 grams were cut if necessary from larger samples in order to be inserted in to the straight tubes. All samples were degassed for more than 1 day at 100° C. before analysis. The samples were then analyzed by adsorption and desorption of $N_2$ gas with a Quantachrome Autosorb IQ (Quantachrome Instruments, Florida, USA) in a 12 mm cell with no bulb and without a rod. Absorption data points are collected from 0.0003 to 0.995 P/P0 and desorption points collected from 0.995 to 0.05 P/P0. The analysis has been duplicated (or triplicated if repeatability was not ideal), and the averaged results reported. The specific surface area S was calculated by the BET method (Details 10 regarding calculation see Autosorb-1 Operating Manual Ver. 1.51 IV. Theory and Discussion; Quantachrome Instruments, Inc.). The total pore volume $V_{liq}$ is derived from the amount of vapor adsorbed at a relative pressure close to unity (p/p0 closest to 1), by assuming that the pores are then filled with liquid adsorbate (Details regarding calculation see Autosorb-1 Operating Manual Ver. 1.51 IV. Theory and Discussion; Quantachrome Instruments, Inc.). The average pore diameter (d) is calculated from the surface area (S) and the total pore volume $V_{liq}$: $d=4V_{liq}/S$. Total pore volume and average pore diameter are reported as determined by Nonlocal Density Functional Theory method.

Method for Measuring Archimedes Density

The measurements were made on a precision balance (identified as "AE 160" from Mettler Instrument Corp., Hightstown, N.J., USA) using a density determination kit (identified as "ME 33360" from Mettler Instrument Corp., Hightstown, N.J.). In this procedure the sample was first weighed in air (A), then immersed in water (B) and weighed. The water was distilled and deionized. One drop of a wetting agent (obtained under trade designation "TERGITOL-TMN-6" from Dow Chemical Co., Danbury, Conn., USA) was added to 250 ml of water. The density was calculated using the formula $\rho=(A/(A-B))\rho 0$, where $\rho 0$ is the density of water. The relative density can be calculated by reference to the theoretical density ($\rho t$) of the material, $\rho rel=(\rho/\rho t)$ 100.

Method for Measuring Flexural Strength of Ceramic Article

The flexural strength was determined according to ISO 6872 (2008). The test piece is printed and processed according to the invention in the shape of a flex bar with approximate dimensions of 1 mm×4 mm×12 mm. Both large faces of the flex bar were polished down to a surface finish from 15 micron grade diamond lapping film (668X Diamond Lapping Film PSA, 3M, St. Paul, Minn.) on a Beta, Grinder-Polisher (Buehler, Lake Bluff, Ill.), operating at 100 rpm and lubricated with water. Each of the 4 edges along the length of the flex bar were chamfered, meaning to create a bevel on the edges of the specimens along, to a 45 degree angle. A 3-point beam bend test configuration with a span of 10.0 mm was employed. The crosshead test speed was 1 mm/min. An Instron 5954 test frame (Instron Corporation, Canton, Mass.) was utilized. A minimum of 5 samples were measured to determine the average strength.

Method for Measuring Translucency of Ceramic Article

If desired, the translucency of the ceramic articles can be evaluated with the following procedure. The test piece is printed and processed as described in the present text in the shape of a disc with approximate dimensions of 1±0.03 mm thick×13 mm diameter. The parallel large faces of the disc were polished down to a surface finish from 15 micron grade diamond lapping film (668X Diamond Lapping Film PSA, 3M, St. Paul, Minn.) on a Beta, Grinder-Polisher (Buehler, Lake Bluff, Ill.), operating at 100 rpm and lubricated with water. The polished sample was measured with a spectrophotometer (X-Rite Color i7, Grand Rapids, USA) in reflectance mode. Translucency (T) is determined according to T=1−RB/RW where RB=reflectance through a ceramic disc on a black substrate and RW=reflectance through the same disc on a white substrate. Higher values of translucency are indicative of greater transmission of light, and less opacity. A minimum of 5 samples were measured to determine the average translucency.

Method for Crystalline Structure and Size (XRD Analysis)

If desired, the crystalline structure of the ceramic articles can be evaluated with the following procedure. Dried zirconia samples are ground by hand using an agate mortar and pestle. A liberal amount of the sample is applied by spatula to a glass microscope slide on which a section of double-sided adhesive tape has been adhered. The sample is pressed into the adhesive on the tape by forcing the sample against the adhesive with the spatula blade. Excess sample is removed by scraping the sample area with the edge of the spatula blade, leaving a thin layer of particles adhered to the adhesive. Loosely adhered materials remaining after the scraping are removed by forcefully tapping the microscope slide against a hard surface. In a similar manner, corundum (Linde 1.0 μm alumina polishing powder, Lot Number C062, Union Carbide, Indianapolis, Ind.) is prepared and used to calibrate the X-ray diffractometer for instrumental broadening.

X-ray diffraction scans are obtained using a Philips vertical diffractometer having a reflection geometry, copper Kα radiation, and a proportional detector registry of the scattered radiation. The diffractometer is fitted with variable incident beam slits, fixed diffracted beam slits, and a graphite diffracted beam monochromator. The survey scan is recorded from 25 to 55 degrees two theta (2θ) using a step size of 0.04 degrees and a dwell time of 8 seconds. X-ray generator settings of 45 kV and 35 mA are used. Data for the corundum standard is collected on three separate areas of several individual corundum mounts. Likewise, data is collected on three separate areas of the thin layer sample mount.

The observed diffraction peaks are identified by comparison to reference diffraction patterns contained within the International Center for Diffraction Data (ICDD) powder diffraction database (sets 1-47, ICDD, Newton Square, Pa., USA). The diffraction peaks for the samples are attributed to either cubic/tetragonal (C/T) or monoclinic (M) forms of zirconia. For zirconia-based particles, the (111) peak for the cubic phase and (101) peak for the tetragonal phase could not be separated so these phases are reported together. The amounts of each zirconia form are evaluated on a relative basis, and the form of zirconia having the most intense diffraction peak is assigned the relative intensity value of 100. The strongest line of the remaining crystalline zirconia form is scaled relative to the most intense line and given a value between 1 and 100.

Peak widths for the observed diffraction maxima due to corundum are measured by profile fitting. The relationship between mean corundum peak widths and corundum peak position (2θ) is determined by fitting a polynomial to these data to produce a continuous function used to evaluate the instrumental breadth at any peak position within the corundum testing range. Peak widths for the observed diffraction maxima due to zirconia are measured by profile fitting the observed diffraction peaks. The following peak widths are evaluated depending on the zirconia phase found to be present:

Cubic/Tetragonal (C/T): (1 1 1)
Monoclinic (M): (−1 1 1), and (1 1 1)

A Pearson VII peak shape model with Kα1 and Kα2 wavelength components and linear background model are used for all measurements. Widths are calculated as the peak full width at half maximum (FWHM) having units of degrees. The profile fitting is accomplished by use of the capabilities of the JADE diffraction software suite. Sample peak widths are evaluated for the three separate data collections obtained for the same thin layer sample mount.

Sample peaks are corrected for instrumental broadening by interpolation of instrumental breadth values from corundum instrument calibration and corrected peak widths converted to units of radians. The Scherrer equation is used to calculate the primary crystal size.

$$\text{Crystallite Size } (D) = K\lambda/\beta(\cos\theta)$$

In the Scherrer equation, K is the form factor (here 0.9), λ is the wavelength (1.540598 Å), β is the calculated peak width after correction for instrumental broadening (in radians), and θ equals half the peak position (scattering angle). β is equal to [calculated peak FWHM−instrumental breadth] (converted to radians) where FWHM is full width at half maximum. The cubic/tetragonal (C/T) mean crystallite size is measured as the average of three measurements using (1 1 1) peak. That is, $$C/T \text{ mean crystallite size} = [D(1\ 1\ 1)_{area1} + D(1\ 1\ 1)_{area2} + D(1\ 1\ 1)_{area3}]/3.$$

The monoclinic (M) crystallite size is measured as the average of three measurements using the
(−1 1 1) peak and three measurements using the (1 1 1) peak.

$$M \text{ mean crystallite size} = [D(-1\ 1\ 1)\text{area } 1 + D(-1\ 1\ 1)\text{area } 2 + D(-1\ 1\ 1)\text{area } 3 + D(1\ 1\ 1)\text{area } 1 + D(1\ 1\ 1)\text{area } 2 + D(1\ 1\ 1)\text{area } 3]/6$$

The weighted average of the cubic/tetragonal (C/T) and monoclinic phases (M) is calculated.

$$\text{Weighted average} = [(\%\ C/T)(C/T \text{ size}) + (\%\ M)(M \text{ size})]/100$$

In this equation, % C/T equals the percent crystallinity contributed by the cubic and tetragonal crystallite content of the $ZrO_2$ particles; C/T size equals the size of the cubic and tetragonal crystallites; % M equals the percent crystallinity contributed by the monoclinic crystallite content of the $ZrO_2$ particles; and M size equals the size of the monoclinic crystallites.

Method for Photon Correlation Spectroscopy (PCS)

If desired, particle size measurements are made using a light scattering particle sizer equipped with a red laser having a 633 nm wavelength of light (obtained under the trade designation "ZETA SIZER—Nano Series, Model ZEN3600" from Malvern Instruments Inc., Westborough, Mass.). Each sample is analyzed in a one-centimeter square polystyrene sample cuvette. The sample cuvette is filled with about 1 gram of deionized water, and then a few drops (about 0.1 gram) of the zirconia-based sol are added. The composition (e.g., sample) within each sample cuvette is mixed by drawing the composition into a clean pipette and discharging the composition back into the sample cuvette several times. The sample cuvette is then placed in the instrument and equilibrated at 25° C. The instrument parameters are set as follows: dispersant refractive index 1.330, dispersant viscosity 0.8872 MPa-second, material refractive index 2.10, and material absorption value 0.10 units. The automatic size-measurement procedure is then run. The instrument automatically adjusted the laser-beam position and attenuator setting to obtain the best measurement of particle size.

The light scattering particle-sizer illuminates the sample with a laser and analyzed the intensity fluctuations of the light scattered from the particles at an angle of 173 degrees. The method of Photon Correlation Spectroscopy (PCS) is used by the instrument to calculate the particle size. PCS uses the fluctuating light intensity to measure Brownian motion of the particles in the liquid. The particle size is then calculated to be the diameter of sphere that moves at the measured speed.

The intensity of the light scattered by the particle is proportional to the sixth power of the particle diameter. The Z-average size or cumulant mean is a mean calculated from the intensity distribution and the calculation is based on assumptions that the particles are mono-modal, mono-disperse, and spherical. Related functions calculated from the fluctuating light intensity are the Intensity Distribution and its mean. The mean of the Intensity Distribution is calculated based on the assumption that the particles are spherical. Both the Z-average size and the Intensity Distribution mean are more sensitive to larger particles than smaller ones.

The Volume Distribution gives the percentage of the total volume of particles corresponding to particles in a given size range. The volume-average size is the size of a particle that corresponds to the mean of the Volume Distribution. Since the volume of a particle is proportional to the third power of the diameter, this distribution is less sensitive to larger particles than the Z-average size. Thus, the volume-average will typically be a smaller value than the Z-average size.

Method for Determining Dispersion Index (DI)

The dispersion index is equal to the volume-average size measured using Photon Correlation Spectroscopy divided by the weighted average crystallite size measured by XRD.

Method for Determining Polydispersity Index (PI)

The polydispersity index is a measure of the breadth of the particle size distribution and is calculated along with the Z-average size in the cumulants analysis of the intensity distribution using Photon Correlation Spectroscopy. For values of the polydispersity index of 0.1 and below, the breadth of the distribution is considered narrow. For values above 0.5, the breadth of the distribution is considered broad and it is unwise to rely on the Z-average size to fully characterize the particle size. Instead, one should characterize the particles using a distribution analysis such as the intensity or volume distribution. The calculations for the Z-average size and polydispersity index are defined in the ISO 13321:1996 E ("Particle size analysis—Photon correlation spectroscopy", International Organization for Standardization, Geneva, Switzerland).

Method for Determining pH-Value

If desired, the measurement of the pH-value can be achieved by means known by the person skilled in art. E.g. an instrument like Metrohm™ 826 can be used.

Method for Measuring Wt.-% Solids

The wt.-% solids can be determined by drying a sample weighing 3-6 grams at 120° C. for 30 min. The percent solids can be calculated from the weight of the wet sample (i.e., weight before drying, $\text{weight}_{wet}$) and the weight of the dry sample (i.e., weight after drying, $\text{weight}_{dry}$) using the following equation: wt-% solids=100 ($\text{weight}_{dry}$)/$\text{weight}_{wet}$.

Method for Measuring Oxide Content

The oxide content of a sol sample can be determined by measuring the percent solids content as described in the "Method for Measuring Wt.-% Solids" then measuring the oxide content of those solids as described in this section.

The oxide content of a solid is measured via thermal gravimetric analysis (obtained under the trade designation "TGA Q500" from TA Instruments, New Castle, Del., USA). The solids (about 50 mg) are loaded into the TGA and the temperature was taken to 900° C. The oxide content of the solid is equal to the residual weight after heating to 900° C.

Method for Determining Vol.-% Oxide

The vol.-% oxide in a sol can be determined by first using a volumetric flask to measure the mass of a known volume of sol, which gives the sol density $\rho_s$ in grams/ml. Then, using the wt.-% oxide (measured as described above in "Method for Measuring Oxide Content"), the vol.-% oxide is calculated as: vol.-% oxide=($\rho_s$*wt.-% oxide)/(oxide density), where a value of 6.05 grams/ml is used for the oxide density.

Method for Determining Viscosity

If desired, the viscosity can be measured using a Brookfield Cone and Plate Viscometer (Model Number DV II available from Brookfield Engineering Laboratories, Middleboro, Mass., USA). The measurements are obtained using spindle CPE-42. The instrument is calibrated with Brookfield Fluid I which gives a measured viscosity of 5.12 mPa*s (cp) at 192 l/sec (50 RPM). The compositions are placed in the measurement chamber. Measurements are made at 3-4 different RPM (revolutions per minute). The measured viscosity is not significantly affected by the shear rate. The shear rate is calculated as 3.84 multiplied by the RPM. Viscosity values, if reported are for the minimum shear rate where the torque is in range.

Method for Determining Light Transmission (% T)

If desired, the light transmission can be measured using a Perkin Elmer Lambda 35 UV/VIS Spectrometer (available from Perkin Elmer Inc., Waltham, Mass., USA). The transmission is measured in a 10-mm quartz cuvette, with a water-filled 10-mm quartz cuvette as the reference. The aqueous $ZrO_2$ sols can be measured at 1 and 10 weight % $ZrO_2$.

Vickers Hardness

If desired, the Vickers hardness can be determined according to ISO 843-4 with the following modifications:

The surface of the samples are ground using silicon carbide grinding paper (P400 and P1200). The test forces are adjusted to the hardness level of samples. Used test forces were between 0.2 kg and 2 kg and were applied for 15 s each indentation. A minimum of 10 indentations is measured to determine the average Vickers hardness. The tests can be conducted with a hardness tester Leco M-400-G (Leco Instrumente GmbH).

A Starting Sol Preparation

Sol compositions are reported in mole percent inorganic oxide. The following hydrothermal reactor was used for preparing the sol. The hydrothermal reactor was prepared from 15 meters of stainless steel braided smooth tube hose (0.64 cm inside diameter, 0.17 cm thick wall; obtained under the trade designation "DuPont T62 CHEMFLUOR PTFE" from Saint-Gobain Performance Plastics, Beaverton, Mich.). This tube was immersed in a bath of peanut oil heated to the desired temperature. Following the reactor tube, a coil of an additional 3 m of the same stainless steel braided smooth tube hose plus 3 m of 0.64 cm stainless-steel tubing with a diameter of 0.64 cm and wall thickness of 0.089 cm that was immersed in an ice-water bath to cool the material and a backpressure regulator valve was used to maintain an exit pressure of 3.45 MPa.

A precursor solution was prepared by combining 2,000 g zirconium acetate solution with 1,889.92 g deionized water. 112.2 g yttrium acetate were added while mixing until fully dissolved. The solids content of the resulting solution was measured gravimetrically (120° C./hr. forced air oven) to be 19.31 wt.-%. 65.28 g deionized water were added to adjust the final concentration to 19 wt.-%. The resulting solution was pumped at a rate of 11.48 ml/min. through the hydrothermal reactor. The temperature was 225° C. and the average residence time was 42 min. A clear and stable zirconia sol was obtained.

The resulting sol was concentrated (35-45 wt.-% solids) via ultrafiltration using a membrane cartridge (obtained under the trade designation "M21S-100-01P" from Spectrum Laboratories Inc., Rancho Dominguez, Calif.). As medium for the filtration process ethanol was used. With that, next to increasing the solid content of the sol, a partial exchange of water with ethanol was achieved.

The size of the obtained zirconia particles was in the range of 15 to 25 nm according to light scattering measurement (Z-average).

B Sol Preparation

A diethylene glycol ethyl ether based sol was produced by adding the appropriate amount of diethylene glycol ethyl ether (adjusted to the intended final concentration of zirconia in the sol, e.g. 50 wt.-%) to the ethanolic sol and afterwards ethanol and water were removed by gentle heating under reduced pressure. Additionally, 2,2,2-MEEAA (2-[2-(2-methoxyethoxy)ethoxy]acetic acid) was added for adjusting the viscosity.

C Printing Sol Preparation 4.3 wt.-% acrylic acid, 2.2 wt.-% hydroxyethylacrylamid (HEAA), 0.08 wt.-% photoinitiator (Irgacure™ 819), 0.02 wt.-% dye (Isatin: 1H-indole-2,3-dione) and 0.02 wt.-% inhibitor (MOP) were added to the sol.

TABLE 1

| Final composition of printing sol | |
|---|---|
| | wt.-% |
| Oxides (96:4 ZrO2:Y2O3 mole) | 50 |
| Acetic acid | 2.4 |
| Diethylene glycol ethyl ether | 38.48 |
| Water | 1 |
| Acrylic acid | 4.3 |
| Hydroxyethylacrylamid | 2.2 |
| Irgacure ™ 819 | 0.08 |
| 2-[2-(2-methoxyethoxy)ethoxy]acetic acid | 1.5 |
| Isatin | 0.02 |
| MOP | 0.02 |

C Processing of Printing Sol

C1 Manufacturing of a Flat Cuboid

The printing sol was processes as follows:

The sol was poured into the working tray of a commercially available SLA/DLP printer (Rapidshape S50; Heimsheim, Germany).

The following conditions were applied:
curing light wavelength: 405 nm light;
exposure time: 2 sec;
layer thickness: 50 μm;
printing protocol: using the standard parameter set for material GP101 (Software: Netfabb Professional for Rapidshape 5.2 64 bit).

The obtained sample was post-cured for 60 sec in a UV light furnace (Heraeus, Germany) and stored in air (FIG. 1A).

The sample was dried applying the following supercritical conditions:
liquid: carbon dioxide;
pressure: 200 bar;
temperature: 100° C.;
duration: 40 h.

Figure 1B:
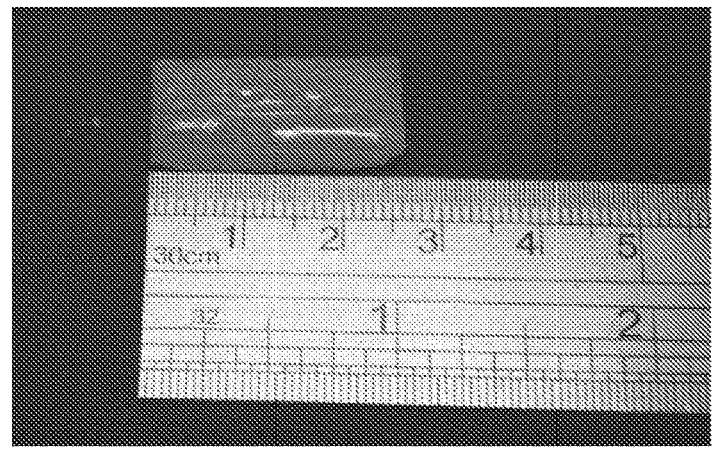
Figure 1C:
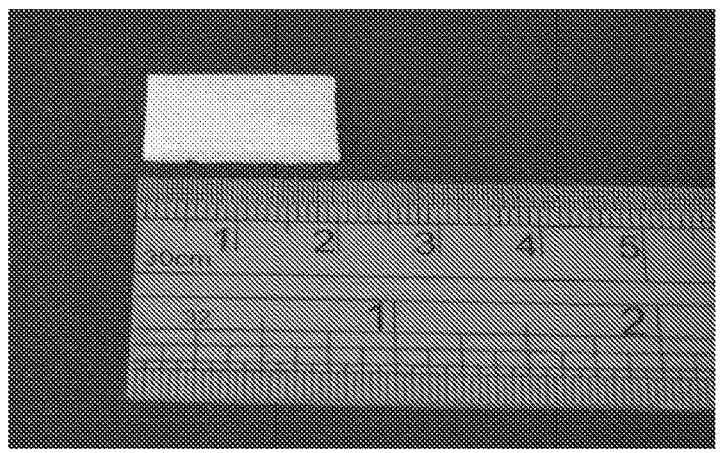

The sample obtained after conducting the supercritical drying step is shown in FIG. 1B, The sample was heated to 1035° C. for 72 h to burnout the remaining organic components. The sample obtained after this burnout and pre-sintering step is shown in FIG. 1C.

Figure 1D:
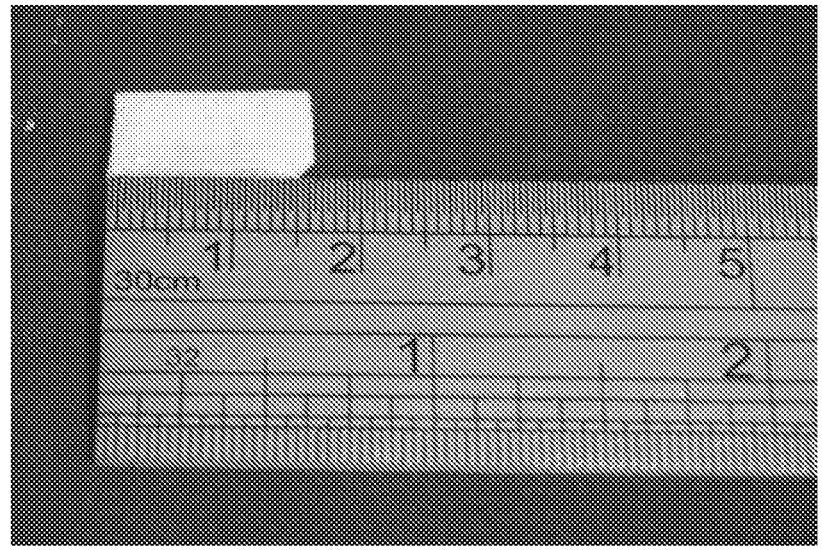

Finally the sample was sintered at 1300° C. for 2 h (FIG. 1D).

The sample did not show any cracks. Further, the sample had a smooth surface.

C2 Manufacturing of a Cube

According to the same process a cuboid (having a different geometry) was manufactured.

Figure 2:
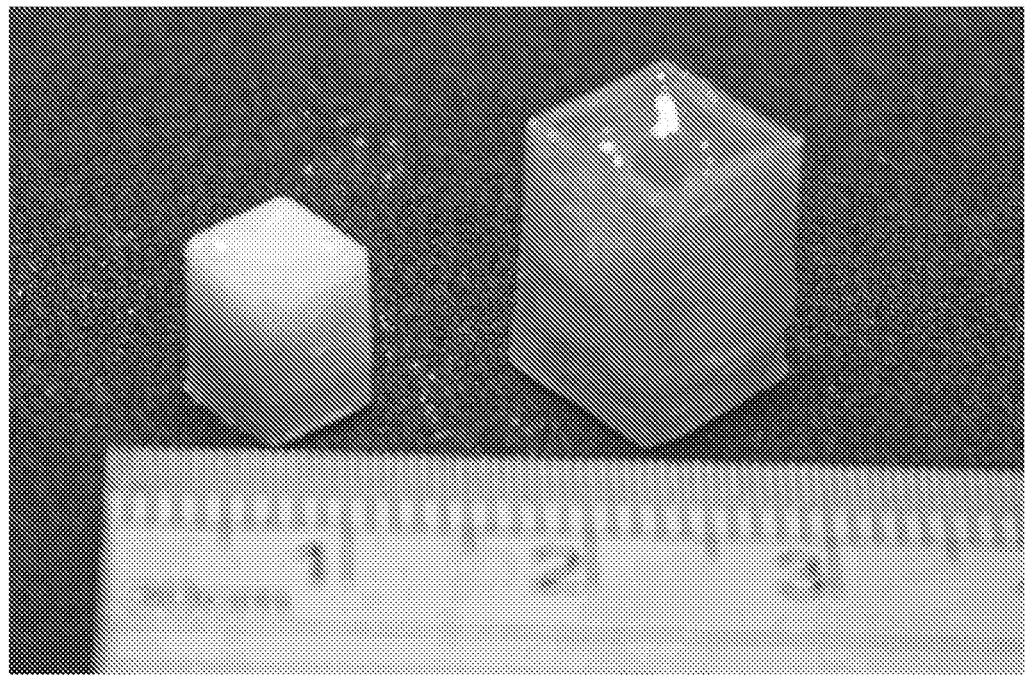
FIG. 2 compares the size of a printed gel-like cuboid with the size of the sintered cuboid ceramic article resulting from this cuboid.

FIG. 2 shows that cuboid after SLA printing (right) and final sintering (left) to visualize the overall volume shrinkage.

D Determination of Volume Shrinkage

A sol containing about 40 wt.-% zirconia nanoparticles, acrylate components and photoinitiator was moulded in a rectangular mould and light cured. The sample had a dimension of 75*44*35 mm.

The sample was super critically dried as described above and measured again. The shrinkage in this step is mainly determined by the amount and nature of the matrix components (acrylates).

In a next step the organic components were burned out and the sample pre-sintered at 1035° C. for 70 h. The shrinkage in this step is mainly regulated by the organic content, the content of zirconia and the homogeneity of the green body. In this step the main shrinkage takes place.

In a final step the sample was sintered at 1300° C. for 2 h until final density was received.

The final shrinkage overall is about 53% linear or about 90% in volume, respectively. The values of volume shrinkage, linear shrinkage and density are listed in Table 2. The relative volume and relative length are calculated based on the Volume F being scaled to 100.

TABLE 2

| Process step | Volume [mm$^3$] | Shrinkage Vol. [%] | Relative volume | Length [mm] | Shrinkage Linear [%] | Relative length | Density [g/cm$^3$] |
|---|---|---|---|---|---|---|---|
| Gel body (Volume A) | 115,500 | — | 1004 | 75 | — | 214 | 0.15 |
| After super critical drying (Volume C) | 86,900 | 25 | 756 | 69 | 8 | 197 | 1 |
| After organic burnout and pre-sintering (Volume E) | 24,200 | 79 | 210 | 45 | 40 | 129 | 2.9 |
| Final sintering (Volume F) | 11,500 | 90 | 100 | 35 | 53 | 100 | 6.05 |

What is claimed is:

1. A process for producing a ceramic article, the process comprising:
    providing a printing sol, wherein the printing sol comprising solvent, nano-sized particles, radiation curable monomer(s) and photoinitiator, and wherein the printing sol having a viscosity of less than 500 mPa*s at 23° C.;
    processing the printing sol as construction material in an additive manufacturing process to obtain a 3-dimensional article being in a gel state, the 3-dimensional article having a Volume A;
    transferring the 3-dimensional article being in a gel state to a 3-dimensional article being in a dry state, namely an aerogel or xerogel; and
    applying a heat treatment step to obtain a sintered 3 ceramic article, the ceramic article having a Volume F;
    wherein Volume A of the 3-dimensional article in a gel state being more than 500% of Volume F of the ceramic article in its sintered state.

2. The process of claim 1, the transfer of the 3-dimensional article being in a gel state to a 3-dimensional article being in a dry state being conducted by applying a supercritical drying step.

3. The process of claim 1, the additive manufacturing process being selected from: stereolithographic printing.

4. The process of claim 1, the additive manufacturing processing comprising:
    providing a layer of the construction material on a surface;
    radiation curing those parts of the layer of construction material which will belong to the 3-dimensional article to be produced;
    providing an additional layer of the construction material in contact with the radiation cured surface of the previous layer; and
    repeating the previous steps until the 3-dimensional article is obtained.

5. The process of claim 1, the process not comprising either or all of the following steps:
    heating the construction material during the additive manufacturing processing step to a temperature above 70° C.;
    applying pressure during the sintering step.

6. The process of claim 1, the printing sol being characterized by at least one or all of the following features:
    being translucent in a wavelength range from 420 to 600 nm for a path length of 10 mm;
    showing a transmission of at least 5% at 420 nm determined for a path length of 10 mm;
    pH value: from 1 to 6.

7. The process of claim 1, the printing sol being characterized by at least one or more or all of the following features:
    the nano-sized particles being present in an amount from 20 to 70 wt.-% with respect to the weight of the printing sol;
    the average primary particle size of the nano-sized zirconia particles being in a range up to 50 nm.

8. The process of claim 1, the nano-sized particles being characterized by at least one or all of the following features:
    being crystalline;
    being essentially spherical, cuboidal or a mixture thereof;
    being non-associated;
    comprising $ZrO_2$ in an amount of 70 to 100 mol-%;
    comprising $HfO_2$ in an amount of 0 to 4.5 mol-%;
    comprising a stabilizer selected from $Y_2O_3$, $CeO_2$, MgO, CaO, $La_2O_3$ or a combination thereof in an amount of 0 to 30 mol-%;
    comprising $Al_2O_3$ in an amount of 0 to 1 mol-%.

9. The process of claim 1, the printing sol comprising in addition organic dye(s).

10. The process of claim 9, the organic dye being characterized by at least one or all of the following features:
    being present in an amount from 0.001 to 0.5 wt.-% with respect to the weight of the printing sol;
    showing a radiation absorption in the range from 200 to 500 nm;

having a molecular weight in the range of 100 to 1,000 g/mol;

being soluble in the solvent;

being combustible without residues at a temperature below 800° C.;

not containing heavy metal ions with an atomic mass above 40.

11. The process of claim 1, the printing sol in addition comprising inhibitor(s), preferably in an amount from 0.001 to 1 wt.-% with respect to the weight of the printing sol.

12. The process of claim 1, the radiation curable monomer(s) being characterized by at least one or all of the following features:

being represented by a formula A-B with A comprising an acidic group, a silane group, an amine, amide or alcohol group and B comprising a vinyl group;

being present in the printing sol in an amount from 2 to 30 wt.-% with respect to the weight of the printing sol.

13. The process of claim 1, the printing sol not comprising either or all of the following components:

wax(es) in an amount of more than 0.1 wt.-%;

insoluble pigment(s) in an amount of more than 0.5 wt.-%;

particles having a primary particle diameter larger than 100 nm in an amount of more than 1 wt.-%;

wt.-% with respect to the weight of the printing sol.

14. A ceramic article obtained by the process of claim 1, the ceramic article being characterized by either or all of the following features:

density: more than 98.5% with respect to theoretical density;

translucency: more than 30% determined on a polished sample having a thickness of 1 mm;

flexural strength: at least 450 MPa according to ISO 6872;

phase content tetragonal phase: from 0 to 100 wt.-%;

phase content cubic phase: from 0 to 100 wt.-%;

dimension in either x, y or z direction: at least 0.25 mm.

15. The ceramic article of claim 14, the ceramic article having the shape of a dental or orthodontic article.

* * * * *